United States Patent
McPhaul et al.

(10) Patent No.: US 12,018,402 B2
(45) Date of Patent: Jun. 25, 2024

(54) METHODS FOR DETECTING INTRACRANIAL NEOPLASMS

(71) Applicant: Quest Diagnostics Investments LLC, Secaucus, NJ (US)

(72) Inventors: Michael J. McPhaul, San Juan Capistrano, CA (US); Heather R. Sanders, Winchester, CA (US)

(73) Assignee: Quest Diagnostics Investments LLC, Secaucus, NJ (US)

( * ) Notice: Subject to any disclaimer, the term of this patent is extended or adjusted under 35 U.S.C. 154(b) by 569 days.

(21) Appl. No.: 16/325,856

(22) PCT Filed: Aug. 17, 2017

(86) PCT No.: PCT/US2017/047316
§ 371 (c)(1),
(2) Date: Feb. 15, 2019

(87) PCT Pub. No.: WO2018/035308
PCT Pub. Date: Feb. 22, 2018

(65) Prior Publication Data
US 2019/0365779 A1 Dec. 5, 2019

Related U.S. Application Data

(60) Provisional application No. 62/376,664, filed on Aug. 18, 2016.

(51) Int. Cl.
| | | |
|---|---|---|
| *C40B 30/04* | (2006.01) | |
| *A61K 31/03* | (2006.01) | |
| *A61K 31/48* | (2006.01) | |
| *A61K 31/567* | (2006.01) | |
| *A61K 31/4174* | (2006.01) | |
| *A61K 31/4439* | (2006.01) | |
| *A61K 31/444* | (2006.01) | |
| *A61K 31/451* | (2006.01) | |
| *A61K 31/496* | (2006.01) | |
| *A61K 31/506* | (2006.01) | |
| *C12Q 1/6806* | (2018.01) | |
| *C12Q 1/6886* | (2018.01) | |

(52) U.S. Cl.
CPC .............. *C40B 30/04* (2013.01); *A61K 31/03* (2013.01); *A61K 31/48* (2013.01); *A61K 31/567* (2013.01); *A61K 31/4174* (2013.01); *A61K 31/4439* (2013.01); *A61K 31/444* (2013.01); *A61K 31/451* (2013.01); *A61K 31/496* (2013.01); *A61K 31/506* (2013.01); *C12Q 1/6806* (2013.01); *C12Q 1/6886* (2013.01); *C12Q 2600/106* (2013.01); *C12Q 2600/156* (2013.01)

(58) Field of Classification Search
CPC ...... A61K 31/567; A61K 31/03; A61K 31/48; A61K 31/4174; A61K 31/4439; A61K 31/444; A61K 31/451; A61K 31/496; A61K 31/506; A61K 45/06; A61K 31/4188; A61K 38/00; C12Q 1/6806; C12Q 1/6886; C12Q 2600/106; C12Q 2600/156

See application file for complete search history.

(56) References Cited

U.S. PATENT DOCUMENTS

2012/0208706 A1  8/2012  Downing et al.

FOREIGN PATENT DOCUMENTS

| WO | WO-2015/022657 A1 | 2/2015 |
|---|---|---|
| WO | WO 2015/168599 A1 | 11/2015 |

OTHER PUBLICATIONS

Gaillard et al., "Craniopharyngioma", https://radiopaedia.org/articles/craniopharyngioma/ available online Dec. 17, 2015 at archive.org.*
Riviere et al. (Nat Genet 44, 934-940 (2012)).*
Vogelstein et al. (Science, Mar. 29, 2013, vol. 339, Issue 6127, pp. 1546-15).*
Thorpe et al. (Nature Reviews Cancer, vol. 15, Jan. 2015, p. 7-24).*
Brastianos et al. (European Journal of Endocrinology, vol. 174, Issue 4, Apr. 2016, pp. R139-R144).*
Brastianos et al. Cancer Discov (2015) 5 (11): 1164-1177.*
International Search Report and Written Opinion dated Jan. 29, 2018, in PCT/US2017/047316.
Cheng et al., "Memorial Sloan Kettering-Integrated Mutation Profiling of Actionable Cancer Targets (MSK-IMPACT)," J. Mol. Diagn., May 1, 2015, 17(3):251-254.
Herrero-Gonzalez et al., "New Routes to Old Places: PIK3R1 and PIK3R2 Join PIK3CA and PTEN as Endometrial Cancer Genes," Cancer Discovery, Jul. 2011, 1(2):106-107.
Mao et al., "Differential expression of microRNAs in GH-secreting pituitary adenomas," Diagnostic Pathology, Dec. 7, 2010, 5(1):79, 1-8.
Riviere et al., "De novo germline and postzygotic mutations in AKT3, PIK3R2 and PIK3CA cause a spectrum of related megalencephaly syndromes," Nat. Genet., Jun. 24, 2012, 44(8):934-940.
Supplementary European Search Report dated Mar. 23, 2020, in EP 17842107.9.
Terrone et al., "De novo PIK3R2 variant causes polymicrogyria, corpus callosum hyperplasia and focal cortical dysplasia," European Journal of Human Genetics, Feb. 10, 2016, 24(9):1359-1362.

(Continued)

*Primary Examiner* — Christian C Boesen
(74) *Attorney, Agent, or Firm* — Foley & Lardner LLP

(57) ABSTRACT

The present technology is related to methods for detecting genetic alterations underlying intracranial neoplasms such as pituitary adenomas, meningiomas, and craniopharyngiomas. The methods disclosed herein are useful in determining whether a patient harboring an intracranial tumor will benefit from or is predicted to be responsive to treatment with an individual therapeutic agent or a specific combination of therapeutic agents. Kits for use in practicing the methods are also provided.

9 Claims, No Drawings

(56) References Cited

OTHER PUBLICATIONS

Office Action and Search Report dated Oct. 31, 2022 in CN 201780062237.4, with English translations.
Xie et al., "Analysis of CCM1 Gene 8th Exon Mutation of Intracranial Cavernous Angiomas an a New 704insT Insertion Site," Fudan University Journal of Medical Sciences, Jun. 9, 2005, 3:280-283, with English abstract.

* cited by examiner

METHODS FOR DETECTING INTRACRANIAL NEOPLASMS

CROSS-REFERENCE TO RELATED APPLICATION

This application is a U.S. National Stage of International Application Number PCT/US2017/047316 filed Aug. 17, 2017, which claims the benefit of and priority to U.S. Provisional Application No. 62/376,664 filed Aug. 18, 2016, the entire disclosure of which is herein incorporated by reference.

TECHNICAL FIELD

The present technology is directed to methods for detecting genetic alterations underlying intracranial neoplasms such as pituitary adenomas, meningiomas, and craniopharyngiomas. The methods disclosed herein are useful in determining whether a patient harboring an intracranial tumor will benefit from or is predicted to be responsive to treatment with an individual therapeutic agent or a specific combination of therapeutic agents. These methods are based on screening a patient's intracranial tumors and detecting alterations in a specific set of intracranial neoplasm-related genes. Kits for use in practicing the methods are also provided.

BACKGROUND

The following description of the background of the present technology is provided simply as an aid in understanding the present technology and is not admitted to describe or constitute prior art to the present technology.

Brain tumors arise as a result of complex interactions of multiple and cumulative genetic alterations and may originate from neural elements within the brain, or they may represent the spread of distant cancers. Primary brain tumors arise from CNS tissue and account for roughly half of all cases of intracranial neoplasms. Gliomas, metastases, meningiomas, pituitary adenomas, and acoustic neuromas account for 95% of all brain tumors.

While meningiomas, pituitary adenomas, and craniopharyngiomas are often benign in nature, they may have a devastating impact on account of their location, growth tendencies, and infiltrative properties. Small, critically located tumors may damage specific neural pathways traversing the brain. Tumors can invade, infiltrate, or supplant normal parenchymal tissue, disrupting normal function. Because the brain dwells in the limited volume of the cranial vault, growth of intracranial tumors with accompanying edema may cause increased intracranial pressure. Tumors adjacent to the third and fourth ventricles may impede the flow of cerebrospinal fluid, leading to obstructive hydrocephalus. In addition, tumors generate new blood vessels (i.e., angiogenesis), disrupting the normal blood-brain barrier and promoting edema.

Knowledge of the molecular mechanisms that drive intracranial neoplasms remains limited, which has hampered the development of systemic therapies for these tumors.

SUMMARY OF THE PRESENT TECHNOLOGY

The present disclosure provides genetic alterations associated with specific types of intracranial neoplasms, which are useful in identifying a tumor's predisposition for metastasis and guiding treatment decisions. Such methods would aid in predicting the responsiveness of individual patients to a particular drug regimen and the identification of optimal therapeutic strategies at the outset. The methods and compositions disclosed herein relate to the detection of mutations that are predictive of the responsiveness of a subject diagnosed with an intracranial neoplasm to a particular therapeutic regimen.

In one aspect, the methods and compositions of the present technology are useful in selecting or designing an optimal therapeutic regimen for a subject harboring an intracranial neoplasm. It is contemplated that the methods disclosed herein allow for rapid and sensitive detection of mutations in BRAF, PIK3R2, CNTNAP1, CTNNB1, SLIT1, NTRK3, HUWE1, CASKIN1, JMJD7, OR51T1, FAM20A, INHBA, OGDH, EPN3, LYPD2, SF3B1, APOD, CATSPER3, SEC16A, OR5T3, TANK, TAS1R3, RBPJL, ADAMTS16, PTAR1, PCDH20, BRCA2, WDR45, ATG4B, ZNF407, H6PD, NF2, BBS12, PSMD12, and TNN.

In some embodiments, the therapeutic regimen comprises one or more of BRAF inhibitors, SF3b complex inhibitors, dopamine agonists, pasireotide (Signifor®), cyproheptadine (Periactin®), steroidogenesis inhibitors, Mifepristone (Korlym®), PI3K/AKT/mTOR pathway inhibitors, GnRH antagonists and WNT signaling pathway inhibitors.

In one aspect, the present disclosure provides a method for detecting at least one genetic mutation in an intracranial tumor of a subject comprising (a) extracting DNA from a fresh or frozen intracranial tumor sample obtained from the subject; (b) extracting DNA from a control tissue sample obtained from the subject; (c) generating a first library from the intracranial tumor sample comprising amplicons corresponding to a first plurality of genes; (d) generating a second library from the control tissue sample comprising amplicons corresponding to a second plurality of genes; (e) ligating a first adapter sequence comprising a first barcode sequence to the ends of the amplicons corresponding to the first plurality of genes; (f) ligating a second adapter sequence comprising a second barcode sequence to the ends of the amplicons corresponding to the second plurality of genes; and (g) detecting at least one genetic mutation in the amplicons corresponding to the first plurality of genes using high throughput massive parallel sequencing, wherein the at least one genetic mutation (i) corresponds to at least one gene selected from the group consisting of: PIK3R2, CNTNAP1, SLIT1, NTRK3, HUWE1, CASKIN1, JMJD7, OR51T1, FAM20A, INHBA, OGDH, EPN3, LYPD2, SF3B1, APOD, CATSPER3, SEC16A, OR5T3, TANK, TAS1R3, RBPJL, ADAMTS16, PTAR1, PCDH20, BRCA2, WDR45, ATG4B, ZNF407, H6PD, NF2, BBS12, PSMD12, and TNN; and (ii) is not detected in the amplicons corresponding to the second plurality of genes.

In some embodiments, the method further comprises detecting a BRAF mutation or a CTNNB1 mutation in the amplicons corresponding to the first plurality of genes, wherein the BRAF mutation or the CTNNB1 mutation is not detected in the amplicons corresponding to the second plurality of genes. In some embodiments, the BRAF mutation is BRAF V600E. In other embodiments, the CTNNB1 mutation is CTNNB1 S37C, CTNNB1 T41I or CTNNB1 S33C.

Additionally or alternatively, in some embodiments of the method, the intracranial tumor is a pituitary adenoma, meningioma, or craniopharyngioma. In certain embodiments, the pituitary adenoma is prolactin-secreting or ACTH-secreting. Additionally or alternatively, in some embodiments, the pituitary adenoma is not associated with a mutation in AIP or MEN1. In some embodiments, the craniopharyngioma is papillary or adamantinomatous.

Additionally or alternatively, in some embodiments of the method, the control tissue sample is a matched whole blood sample from the subject.

In some embodiments of the method, the high throughput massive parallel sequencing is performed using pyrosequencing, reversible dye-terminator sequencing, SOLiD sequencing, Ion semiconductor sequencing, Helioscope single molecule sequencing, sequencing by synthesis, sequencing by ligation, or SMRT™ sequencing.

In some embodiments of the method, the first adapter sequence and/or the second adapter sequence is a P5 adapter, P7 adapter, P1 adapter, A adapter, or Ion Xpress™ barcode adapter.

Additionally or alternatively, in some embodiments of the method, the at least one genetic mutation detected is PIK3R2 E593K, CNTNAP1 R270Q, SLIT1 H566R, NTRK3 V221I, HUWE1 S2039F, CASKIN1 P1196L, JMJD7 L185F, OR51T1 R329H, FAM20A S119R, INHBA P291S, OGDH I446F, EPN3 D458E, LYPD2 R24C, SF3B1 R625C, APOD D144Y, CATSPER3 E304A, SEC16A G1091R, OR5T3 L144H, TANK R394Q, TAS1R3 D307H, RBPJL L181P, ADAMTS16 P870S, PTAR1 D89A, PCDH20 D773H, BRCA2 P3067L, WDR45 R280C, ATG4B R49G, ZNF407 C120Y, H6PD P725T, NF2 Q324*, BBS12 R431P, PSMD12 I66V, or TNN L278V.

In one aspect, the present disclosure provides a method of detecting the presence of at least one actionable genetic mutation in an intracranial tumor of a subject comprising (a) contacting a nucleic acid obtained from an intracranial tumor sample with at least one primer pair that amplifies at least one gene selected from PIK3R2, CNTNAP1, SLIT1, NTRK3, HUWE1, CASKIN1, JMJD7, OR51T1, FAM20A, INHBA, OGDH, EPN3, LYPD2, SF3B1, APOD, CATSPER3, SEC16A, OR5T3, TANK, TAS1R3, RBPJL, ADAMTS16, PTAR1, PCDH20, BRCA2, WDR45, ATG4B, ZNF407, H6PD, NF2, BBS12, PSMD12, and TNN; and (b) detecting at least one allelic variant in the nucleic acid, wherein the at least one allelic variant is selected from the group consisting of PIK3R2 E593K, CNTNAP1 R270Q, SLIT1 H566R, NTRK3 V221I, HUWE1 S2039F, CASKIN1 P1196L, JMJD7 L185F, OR51T1 R329H, FAM20A S119R, INHBA P291S, OGDH I446F, EPN3 D458E, LYPD2 R24C, SF3B1 R625C, APOD D144Y, CATSPER3 E304A, SEC16A G1091R, OR5T3 L144H, TANK R394Q, TAS1R3 D307H, RBPJL L181P, ADAMTS16 P870S, PTAR1 D89A, PCDH20 D773H, BRCA2 P3067L, WDR45 R280C, ATG4B R49G, ZNF407 C120Y, H6PD P725T, NF2 Q324*, BBS12 R431P, PSMD12 I66V, and TNN L278V, wherein detecting the at least one allelic variant is indicative of the presence of an actionable genetic mutation in the intracranial tumor of the subject.

In another aspect, the present disclosure provides a method of detecting the presence of at least one actionable genetic mutation in an intracranial tumor of a subject comprising (a) contacting a nucleic acid obtained from an intracranial tumor sample with one or more probes that hybridize to at least one gene selected from PIK3R2, CNTNAP1, SLIT1, NTRK3, HUWE1, CASKIN1, JMJD7, OR51T1, FAM20A, INHBA, OGDH, EPN3, LYPD2, SF3B1, APOD, CATSPER3, SEC16A, OR5T3, TANK, TAS1R3, RBPJL, ADAMTS16, PTAR1, PCDH20, BRCA2, WDR45, ATG4B, ZNF407, H6PD, NF2, BBS12, PSMD12, and TNN; wherein the one or more probes can recognize and discriminate allelic variants of PIK3R2, CNTNAP1, SLIT NTRK3, HUWE1, CASKIN1, JMJD7, OR51T1, FAM20A, INHBA, OGDH, EPN3, LYPD2, SF3B1, APOD, CATSPER3, SEC16A, OR5T3, TANK, TAS1R3, RBPJL, ADAMTS16, PTAR1, PCDH20, BRCA2, WDR45, ATG4B, ZNF407, H6PD, NF2, BBS12, PSMD12, and TNN; and (b) detecting at least one allelic variant in the nucleic acid, wherein the at least one allelic variant is selected from the group consisting of PIK3R2 E593K, CNTNAP1 R270Q, SLIT1 H566R, NTRK3 V221I, HUWE1 S2039F, CASKIN1 P1196L, JMJD7 L185F, OR51T1 R329H, FAM20A S119R, INHBA P291 S, OGDH I446F, EPN3 D458E, LYPD2 R24C, SF3B1 R625C, APOD D144Y, CATSPER3 E304A, SEC16A G1091R, OR5T3 L144H, TANK R394Q, TAS1R3 D307H, RBPJL L181P, ADAMTS16 P870S, PTAR1 D89A, PCDH20 D773H, BRCA2 P3067L, WDR45 R280C, ATG4B R49G, ZNF407 C120Y, H6PD P725T, NF2 Q324*, BBS12 R431P, PSMD12 I66V, and TNN L278V, wherein detecting the at least one allelic variant is indicative of the presence of an actionable genetic mutation in the intracranial tumor of the subject.

Additionally or alternatively, in any of the above embodiments, the methods further comprise detecting BRAF V600E, CTNNB1 S37C, CTNNB1 T41I or CTNNB1 S33C in the nucleic acid.

In one aspect, the present disclosure provides a method for selecting a subject with an intracranial neoplasm for treatment with one or more chemotherapeutic agents comprising (a) extracting DNA from a fresh or frozen intracranial tumor sample obtained from the subject; (b) generating a DNA library from the intracranial tumor sample, wherein the DNA library comprises amplicons corresponding to a plurality of genes; (c) detecting at least one genetic mutation in at least one of the amplicons; and (d) selecting the subject for treatment with one or more chemotherapeutic agents, if a mutation in at least one of the amplicons corresponding to at least one gene selected from PIK3R2, CNTNAP1, SLIT1, NTRK3, HUWE1, CASKIN1, JMJD7, OR51T1, FAM20A, INHBA, OGDH, EPN3, LYPD2, SF3B1, APOD, CATSPER3, SEC16A, OR5T3, TANK, TAS1R3, RBPJL, ADAMTS16, PTAR1, PCDH20, BRCA2, WDR45, ATG4B, ZNF407, H6PD, NF2, BBS12, PSMD12, and TNN is detected, wherein the one or more chemotherapeutic agents are selected from a BRAF inhibitor, a SF3b complex inhibitor, a dopamine agonist, pasireotide (Signifor®), cyproheptadine (Periactin®), a steroidogenesis inhibitor, Mifepristone (Korlym®), a PI3K/AKT/mTOR pathway inhibitor and a WNT signaling pathway inhibitor. In some embodiments of the method, the subject harbors an additional mutation selected from the group consisting of BRAF V600E, CTNNB1 S37C, CTNNB1 T41I and CTNNB1 S33C.

Additionally or alternatively, in some embodiments of the method, the BRAF inhibitor is selected from the group consisting of GDC-0879, SB590885, Encorafenib, RAF265, TAK-632, PLX4720, CEP-32496, AZ628, Sorafenib Tosylate, Sorafenib, Vemurafenib (Zelboraf) and Dabrafenib (GSK2118436). In certain embodiments, the SF3b complex inhibitor is spliceostatin A. In some embodiments of the method, the dopamine agonist is cabergoline or bromocriptine. In other embodiments of the method, the steroidogenesis inhibitor is ketoconazole, aminoglutethimide, etomidate, metyrapone, or mitotane. In some embodiments of the method, the WNT signaling pathway inhibitor is ICG-001, iCRT3, iCRT5, iCRT14, BC21, NC043 (15-oxospiramilactone), PKF115-584, CGP049090, PKF118-310, Thiazolidinediones (A2TG and STG28), Murrayafoline A, OSU03012, 3,6-dihydroxyflavone, PNU-7465431, CCT036477, CCT070535, CCT031374, or a non-steroidal anti-inflammatory drug. In some embodiments of the method, the PI3K/

AKT/mTOR pathway inhibitor is selected from the group consisting of BKM120, BEZ235, Pictilisib (GDC-0941), LY294002, CAL-101 (Idelalisib), GNE-317, PI-3065, HS-173, PI-103, NU7441, GSK2636771, VS-5584, CZC24832, Duvelisib, TG100-115, A66, YM201636, CAY10505, GSK1059615, PF-04691502, PIK-75, PIK-93, AS-605240, BGT226, AZD6482, Voxtalisib, Alpelisib, CUDC-907, IC-87114, Omipalisib, TG100713, Gedatolisib, CH5132799, PKI-402, BAY 80-6946, TGX-221, XL147, PIK-90, PIK-293, PIK-294, 3-Methyladenine, Quercetin, Wortmannin, ZSTK474, AS-252424, AS-604850, everolimus, and Apitolisib.

Additionally or alternatively, in some embodiments of the method, the intracranial tumor sample is a pituitary adenoma, meningioma, or craniopharyngioma. In certain embodiments, the pituitary adenoma is prolactin-secreting or ACTH-secreting. Additionally or alternatively, in some embodiments, the pituitary adenoma is not associated with a mutation in AIP or MEN1. In some embodiments, the craniopharyngioma is papillary or adamantinomatous.

Additionally or alternatively, in some embodiments of the method, the at least one genetic mutation detected is PIK3R2 E593K, CNTNAP1 R270Q, SLIT1 H566R, NTRK3 V221I, HUWE1 S2039F, CASKIN1 P1196L, JMJD7 L185F, OR51T1 R329H, FAM20A S119R, INHBA P291S, OGDH I446F, EPN3 D458E, LYPD2 R24C, SF3B1 R625C, APOD D144Y, CATSPER3 E304A, SEC16A G1091R, OR5T3 L144H, TANK R394Q, TAS1R3 D307H, RBPJL L181P, ADAMTS16 P870S, PTAR1 D89A, PCDH20 D773H, BRCA2 P3067L, WDR45 R280C, ATG4B R49G, ZNF407 C120Y, H6PD P725T, NF2 Q324*, BBS12 R431P, PSMD12 I66V, or TNN L278V.

In another aspect, the present disclosure provides a method for selecting a subject with an intracranial neoplasm for treatment with a PI3K/AKT/mTOR pathway inhibitor and a BRAF inhibitor comprising: (a) extracting DNA from a fresh or frozen intracranial tumor sample obtained from the subject; (b) generating a DNA library from the intracranial tumor sample, wherein the DNA library comprises amplicons corresponding to a plurality of genes; (c) detecting at least one mutation in at least one of the amplicons; and (d) selecting the subject for treatment with a PI3K/AKT/mTOR pathway inhibitor and a BRAF inhibitor, if a mutation in at least one of the amplicons corresponding to PIK3R2 and a mutation in at least one of the amplicons corresponding to BRAF are detected. In some embodiments of the method, the intracranial neoplasm is a craniopharyngioma.

In some embodiments of the method, the PI3K/AKT/mTOR pathway inhibitor is selected from the group consisting of BKM120, BEZ235, Pictilisib (GDC-0941), LY294002, CAL-101 (Idelalisib), GNE-317, PI-3065, HS-173, PI-103, NU7441, GSK2636771, VS-5584, CZC24832, Duvelisib, TG100-115, A66, YM201636, CAY10505, GSK1059615, PF-04691502, PIK-75, PIK-93, AS-605240, BGT226, AZD6482, Voxtalisib, Alpelisib, CUDC-907, IC-87114, Omipalisib, TG100713, Gedatolisib, CH5132799, PKI-402, BAY 80-6946, TGX-221, XL147, PIK-90, PIK-293, PIK-294, 3-Methyladenine, Quercetin, Wortmannin, ZSTK474, AS-252424, AS-604850, everolimus, and Apitolisib.

In certain embodiments of the method, the BRAF inhibitor is selected from the group consisting of GDC-0879, SB590885, Encorafenib, RAF265, TAK-632, PLX4720, CEP-32496, AZ628, Sorafenib Tosylate, Sorafenib, Vemurafenib (Zelboraf) and Dabrafenib (GSK2118436).

In another aspect, the present disclosure provides a method for selecting a subject with an intracranial neoplasm for treatment with a WNT signaling pathway inhibitor and a GnRH antagonist comprising: (a) extracting DNA from a fresh or frozen intracranial tumor sample obtained from the subject; (b) generating a DNA library from the intracranial tumor sample, wherein the DNA library comprises amplicons corresponding to a plurality of genes; (c) detecting at least one mutation in at least one of the amplicons; and (d) selecting the subject for treatment with a WNT signaling pathway inhibitor and a GnRH antagonist, if a mutation in at least one of the amplicons corresponding to CTNNB1 and a mutation in at least one of the amplicons corresponding to INHBA are detected. In some embodiments of the method, the intracranial neoplasm is a craniopharyngioma.

In certain embodiments of the method, the WNT signaling pathway inhibitor is ICG-001, iCRT3, iCRT5, iCRT14, BC21, NC043 (15-oxospiramilactone), PKF115-584, CGP049090, PKF118-310, Thiazolidinediones (A2TG and STG28), Murrayafoline A, OSU03012, 3,6-dihydroxyflavone, PNU-7465431, CCT036477, CCT070535, CCT031374, or a non-steroidal anti-inflammatory drug.

In some embodiments of the method, the GnRH antagonist is cetrorelix, ganirelix, abarelix, degarelix, elagolix, relugolix (TAK-385), KLH-2109, or ASP-1707.

In one aspect, the present disclosure provides a method for predicting the likelihood of responsiveness of a subject with a pituitary adenoma to treatment with a SF3b complex inhibitor comprising: (a) extracting DNA from a fresh or frozen intracranial tumor sample obtained from the subject; (b) generating a DNA library from the intracranial tumor sample, wherein the DNA library comprises amplicons corresponding to a plurality of genes; (c) detecting at least one mutation in at least one of the amplicons; and (d) identifying the subject as having a high likelihood of responsiveness to treatment with a SF3b complex inhibitor, when a mutation in at least one of the amplicons corresponding to SF3B1 is detected. In some embodiments, the pituitary adenoma is prolactin-secreting or ACTH-secreting. Additionally or alternatively, in some embodiments, the pituitary adenoma is not associated with a mutation in AIP or MEN1.

In some embodiments, the SF3b complex inhibitor is spliceostatin A.

DETAILED DESCRIPTION

The present disclosure provides methods for determining whether a patient harboring an intracranial neoplasm, such as a pituitary adenoma, meningioma, or craniopharyngioma will benefit from or is predicted to be responsive to treatment with an individual therapeutic agent or a specific combination of therapeutic agents. These methods are based on screening a patient's intracranial tumors and detecting alterations in target nucleic acid sequences corresponding to a specific set of genes selected from among BRAF, PIK3R2, CNTNAP1, CTNNB1, SLIT1, NTRK3, HUWE1, CASKIN1, JMJD7, OR51T1, FAM20A, INHBA, OGDH, EPN3, LYPD2, SF3B1, APOD, CATSPER3, SEC16A, OR5T3, TANK, TAS1R3, RBPJL, ADAMTS16, PTAR1, PCDH20, BRCA2, WDR45, ATG4B, ZNF407, H6PD, NF2, BBS12, PSMD12, and TNN. Kits for use in practicing the methods are also provided.

Tumors affecting the pituitary gland and surrounding areas of the central nervous system are among the most frequent intracranial neoplasms. Although these tumors are usually not malignant, their location, growth tendencies, and infiltrative properties can be hazardous to the patient. For example, craniopharyngiomas typically grow at the base of the skull near the pituitary gland and may compress parts of the brain during enlargement, thereby causing vision and learning deficits, endocrine dysfunction, and morbid obesity. Current treatment options for intracranial neoplasms include surgical excision and radiation, which can result in serious, long-lasting side effects in the patient.

Molecular profiling of tumors is becoming increasingly important in the management of advanced cancer. NGS is widely used in cancer research and has become an attractive diagnostic technology in clinical laboratories because of its ability to detect multiple variants in a single assay. One objective of the present technology was to identify and characterize genetic mutations that are associated with different types of intracranial neoplasms that are currently, or are likely to become, therapeutically actionable in intracranial neoplasms. The methods disclosed herein provide additional insights into how different signaling pathways are impacted in different intracranial tumor types, e.g., pituitary adenomas, meningiomas, and craniopharyngiomas.

The methods disclosed herein are useful in (a) predicting the responsiveness of a subject with an intracranial neoplasm to a particular therapeutic agent, and (b) selecting optimal treatment strategies for the subject in light of the molecular profile of the subject's tumor.

Definitions

As used herein, the term "about" in reference to a number is generally taken to include numbers that fall within a range of 1%-5% in either direction (greater than or less than) of the number unless otherwise stated or otherwise evident from the context.

As used herein, the term "actionable genetic mutations" refers to mutations that are associated with (1) treatment with an FDA approved drug, (2) a guideline supported drug treatment, (3) a guideline indication of sensitivity or resistance to a particular treatment, (4) ongoing clinical trials, (5) clinical data supporting an indication of resistance or sensitivity to drug treatment, (6) pre-clinical data showing strong evidence of resistance or sensitivity to a targeted treatment, or (6) a prognostic implication that may guide a physician's treatment decisions.

The term "adapter" refers to a short, chemically synthesized, nucleic acid sequence which can be used to ligate to the end of a nucleic acid sequence in order to facilitate attachment to another molecule. The adapter can be single-stranded or double-stranded. An adapter can incorporate a short (typically less than 50 base pairs) sequence useful for PCR amplification or sequencing.

As used herein, an "alteration" of a gene or gene product (e.g., a marker gene or gene product) refers to the presence of a mutation or mutations within the gene or gene product, e.g., a mutation, which affects the quantity or activity of the gene or gene product, as compared to the normal or wild-type gene. The genetic alteration can result in changes in the quantity, structure, and/or activity of the gene or gene product in a cancer tissue or cancer cell, as compared to its quantity, structure, and/or activity, in a normal or healthy tissue or cell (e.g., a control). For example, an alteration which is associated with cancer, or predictive of responsiveness to anti-cancer therapeutics, can have an altered nucleotide sequence (e.g., a mutation), amino acid sequence, chromosomal translocation, intra-chromosomal inversion, copy number, expression level, protein level, protein activity, in a cancer tissue or cancer cell, as compared to a normal, healthy tissue or cell. Exemplary mutations include, but are not limited to, point mutations (e.g., silent, missense, or nonsense), deletions, insertions, inversions, linking mutations, duplications, translocations, inter- and intra-chromosomal rearrangements. Mutations can be present in the coding or non-coding region of the gene. In certain embodiments, the alterations are associated with a phenotype, e.g., a cancerous phenotype (e.g., one or more of brain cancer risk, brain cancer progression, cancer treatment or resistance to cancer treatment). In one embodiment, the alteration is associated with one or more of: a genetic risk factor for a brain neoplasm, a positive treatment response predictor, a negative treatment response predictor, a positive prognostic factor, a negative prognostic factor, or a diagnostic factor.

As used herein, the terms "amplify" or "amplification" with respect to nucleic acid sequences, refer to methods that increase the representation of a population of nucleic acid sequences in a sample. Nucleic acid amplification methods are well known to the skilled artisan and include ligase chain reaction (LCR), ligase detection reaction (LDR), ligation followed by Q-replicase amplification, PCR, primer extension, strand displacement amplification (SDA), hyper-branched strand displacement amplification, multiple displacement amplification (MDA), nucleic acid strand-based amplification (NASBA), two-step multiplexed amplifications, rolling circle amplification (RCA), recombinase-polymerase amplification (RPA)(TwistDx, Cambridge, UK), transcription mediated amplification, signal mediated amplification of RNA technology, loop-mediated isothermal amplification of DNA, helicase-dependent amplification, single primer isothermal amplification, and self-sustained sequence replication (3SR), including multiplex versions or combinations thereof. Copies of a particular nucleic acid sequence generated in vitro in an amplification reaction are called "amplicons" or "amplification products."

The terms "cancer" or "tumor" are used interchangeably and refer to the presence of cells possessing characteristics typical of cancer-causing cells, such as uncontrolled proliferation, immortality, metastatic potential, rapid growth and proliferation rate, and certain characteristic morphological features. Cancer cells are often in the form of a tumor, but such cells can exist alone within an animal, or can be a non-tumorigenic cancer cell. As used herein, the term "cancer" includes premalignant, as well as malignant cancers.

The terms "complementary" or "complementarity" as used herein with reference to polynucleotides (i.e., a sequence of nucleotides such as an oligonucleotide or a target nucleic acid) refer to the base-pairing rules. The complement of a nucleic acid sequence as used herein refers to an oligonucleotide which, when aligned with the nucleic acid sequence such that the 5' end of one sequence is paired with the 3' end of the other, is in "antiparallel association." For example, the sequence "5'-A-G-T-3'" is complementary to the sequence "3'-T-C-A-5." Certain bases not commonly found in naturally-occurring nucleic acids may be included in the nucleic acids described herein. These include, for example, inosine, 7-deazaguanine, Locked Nucleic Acids (LNA), and Peptide Nucleic Acids (PNA). Complementarity need not be perfect; stable duplexes may contain mismatched base pairs, degenerative, or unmatched bases. Those skilled in the art of nucleic acid technology can determine duplex stability empirically considering a number of variables including, for example, the length of the oligonucleotide, base composition and sequence of the oligonucleotide, ionic strength and incidence of mismatched base pairs. A complement sequence can also be an RNA sequence complementary to the DNA sequence or its complement sequence, and can also be a cDNA.

As used herein, a "control" is an alternative sample used in an experiment for comparison purpose. A control can be "positive" or "negative." A "control nucleic acid sample" or "reference nucleic acid sample" as used herein, refers to nucleic acid molecules from a control or reference sample. In certain embodiments, the reference or control nucleic acid sample is a wild type or a non-mutated DNA or RNA sequence. In certain embodiments, the reference nucleic acid sample is purified or isolated (e.g., it is removed from its natural state). In other embodiments, the reference nucleic acid sample is from a non-tumor sample, e.g., a blood control, a normal adjacent tumor (NAT), or any other non-cancerous sample from the same or a different subject.

"Detecting" as used herein refers to determining the presence of a mutation or alteration in a nucleic acid of interest in a sample. Detection does not require the method to provide 100% sensitivity. Analysis of nucleic acid markers can be performed using techniques known in the art including, but not limited to, sequence analysis, and electrophoretic analysis. Non-limiting examples of sequence analysis include Maxam-Gilbert sequencing, Sanger sequencing, capillary array DNA sequencing, thermal cycle sequencing (Sears et al., *Biotechniques,* 13:626-633 (1992)), solid-phase sequencing (Zimmerman et al., *Methods Mol. Cell Biol,* 3:39-42 (1992)), sequencing with mass spectrometry such as matrix-assisted laser desorption/ionization time-of-flight mass spectrometry (MALDI-TOF/MS; Fu et al., *Nat. Biotechnol,* 16:381-384 (1998)), and sequencing by hybridization. Chee et al., *Science,* 274:610-614 (1996); Drmanac et al., *Science,* 260:1649-1652 (1993); Drmanac et al., *Nat. Biotechnol,* 16:54-58 (1998). Non-limiting examples of electrophoretic analysis include slab gel electrophoresis such as agarose or polyacrylamide gel electrophoresis, capillary electrophoresis, and denaturing gradient gel electrophoresis. Additionally, next generation sequencing methods can be performed using commercially available kits and instruments from companies such as the Life Technologies/Ion Torrent PGM or Proton, the Illumina HiSEQ or MiSEQ, and the Roche/454 next generation sequencing system.

"Detectable label" as used herein refers to a molecule or a compound or a group of molecules or a group of compounds used to identify a nucleic acid or protein of interest. In some embodiments, the detectable label may be detected directly. In other embodiments, the detectable label may be a part of a binding pair, which can then be subsequently detected. Signals from the detectable label may be detected by various means and will depend on the nature of the detectable label. Detectable labels may be isotopes, fluorescent moieties, colored substances, and the like. Examples of means to detect detectable labels include but are not limited to spectroscopic, photochemical, biochemical, immunochemical, electromagnetic, radiochemical, or chemical means, such as fluorescence, chemifluorescence, or chemiluminescence, or any other appropriate means.

As used herein, the term "effective amount" refers to a quantity sufficient to achieve a desired therapeutic and/or prophylactic effect, e.g., an amount which results in the prevention of, or a decrease in a disease or disorder or one or more signs or symptoms associated with a disease or disorder (e.g., intracranial neoplasm). In the context of therapeutic or prophylactic applications, the amount of a composition administered to the subject will depend on the degree, type, and severity of the disease and on the characteristics of the individual, such as general health, age, sex, body weight and tolerance to drugs. The skilled artisan will be able to determine appropriate dosages depending on these and other factors. The compositions can also be administered in combination with one or more additional therapeutic compounds. In the methods described herein, the therapeutic compounds may be administered to a subject having one or more signs or symptoms of a disease or disorder. As used herein, a "therapeutically effective amount" of a compound refers to compound levels in which the physiological effects of a disease or disorder are, at a minimum, ameliorated.

"Gene" as used herein refers to a DNA sequence that comprises regulatory and coding sequences necessary for the production of an RNA, which may have a non-coding function (e.g., a ribosomal or transfer RNA) or which may include a polypeptide or a polypeptide precursor. The RNA or polypeptide may be encoded by a full length coding sequence or by any portion of the coding sequence so long as the desired activity or function is retained. Although a sequence of the nucleic acids may be shown in the form of DNA, a person of ordinary skill in the art recognizes that the corresponding RNA sequence will have a similar sequence with the thymine being replaced by uracil, i.e., "T" is replaced with "U."

The term "hybridize" as used herein refers to a process where two substantially complementary nucleic acid strands (at least about 65% complementary over a stretch of at least 14 to 25 nucleotides, at least about 75%, or at least about 90% complementary) anneal to each other under appropriately stringent conditions to form a duplex or heteroduplex through formation of hydrogen bonds between complementary base pairs. Hybridizations are typically and preferably conducted with probe-length nucleic acid molecules, preferably 15-100 nucleotides in length, more preferably 18-50 nucleotides in length. Nucleic acid hybridization techniques are well known in the art. See, e.g., Sambrook, et al., 1989, *Molecular Cloning: A Laboratory Manual*, Second Edition, Cold Spring Harbor Press, Plainview, N.Y. Hybridization and the strength of hybridization (i.e., the strength of the association between the nucleic acids) is influenced by such factors as the degree of complementarity between the nucleic acids, stringency of the conditions involved, and the thermal melting point ($T_m$) of the formed hybrid. Those skilled in the art understand how to estimate and adjust the stringency of hybridization conditions such that sequences having at least a desired level of complementarity will stably hybridize, while those having lower complementarity will not. For examples of hybridization conditions and parameters, see, e.g., Sambrook, et al., 1989, *Molecular Cloning: A Laboratory Manual*, Second Edition, Cold Spring Harbor Press, Plainview, N.Y.; Ausubel, F. M. et al. 1994, *Current Protocols in Molecular Biology*, John Wiley & Sons, Secaucus, N.J. In some embodiments, specific hybridization occurs under stringent hybridization conditions. An oligonucleotide or polynucleotide (e.g., a probe or a primer) that is specific for a target nucleic acid will "hybridize" to the target nucleic acid under suitable conditions.

As used herein, the terms "individual", "patient", or "subject" are used interchangeably and refer to an individual organism, a vertebrate, a mammal, or a human. In a preferred embodiment, the individual, patient or subject is a human.

As used herein, the term "library" refers to a collection of nucleic acid sequences, e.g., a collection of nucleic acids derived from whole genomic, subgenomic fragments, cDNA, cDNA fragments, RNA, RNA fragments, or a combination thereof. In one embodiment, a portion or all of the library nucleic acid sequences comprises an adapter sequence. The adapter sequence can be located at one or both ends. The adapter sequence can be useful, e.g., for a sequencing method (e.g., an NGS method), for amplification, for reverse transcription, or for cloning into a vector.

The library can comprise a collection of nucleic acid sequences, e.g., a target nucleic acid sequence (e.g., a brain tumor nucleic acid sequence), a reference nucleic acid sequence, or a combination thereof. In some embodiments, the nucleic acid sequences of the library can be derived from a single subject. In other embodiments, a library can comprise nucleic acid sequences from more than one subject (e.g., 2, 3, 4, 5, 6, 7, 8, 9, 10, 20, 30 or more subjects). In some embodiments, two or more libraries from different subjects can be combined to form a library having nucleic acid sequences from more than one subject. In one embodiment, the subject is a human with an intracranial neoplasm such as a pituitary adenoma, meningioma, or craniopharyngioma.

A "library nucleic acid sequence" refers to a nucleic acid molecule, e.g., a DNA, RNA, or a combination thereof, that is a member of a library. Typically, a library nucleic acid sequence is a DNA molecule, e.g., genomic DNA or cDNA. In some embodiments, a library nucleic acid sequence is fragmented, e.g., sheared or enzymatically prepared, genomic DNA. In certain embodiments, the library nucleic acid sequences comprise sequence from a subject and sequence not derived from the subject, e.g., adapter sequence, a primer sequence, or other sequences that allow for identification, e.g., "barcode" sequences.

The term "multiplex PCR" as used herein refers to amplification of two or more PCR products or amplicons which are each primed using a distinct primer pair.

"Next-generation sequencing or NGS" as used herein, refers to any sequencing method that determines the nucleotide sequence of either individual nucleic acid molecules (e.g., in single molecule sequencing) or clonally expanded proxies for individual nucleic acid molecules in a high throughput parallel fashion (e.g., greater than $10^3$, $10^4$, $10^5$ or more molecules are sequenced simultaneously). In one embodiment, the relative abundance of the nucleic acid species in the library can be estimated by counting the relative number of occurrences of their cognate sequences in the data generated by the sequencing experiment. Next generation sequencing methods are known in the art, and are described, e.g., in Metzker, M. *Nature Biotechnology Reviews* 11:31-46 (2010).

As used herein, "oligonucleotide" refers to a molecule that has a sequence of nucleic acid bases on a backbone comprised mainly of identical monomer units at defined intervals. The bases are arranged on the backbone in such a way that they can bind with a nucleic acid having a sequence of bases that are complementary to the bases of the oligonucleotide. The most common oligonucleotides have a backbone of sugar phosphate units. A distinction may be made between oligodeoxyribonucleotides that do not have a hydroxyl group at the 2' position and oligoribonucleotides that have a hydroxyl group at the 2' position. Oligonucleotides may also include derivatives, in which the hydrogen of the hydroxyl group is replaced with organic groups, e.g., an allyl group. Oligonucleotides of the method which function as primers or probes are generally at least about 10-15 nucleotides long and more preferably at least about 15 to 25 nucleotides long, although shorter or longer oligonucleotides may be used in the method. The exact size will depend on many factors, which in turn depend on the ultimate function or use of the oligonucleotide. The oligonucleotide may be generated in any manner, including, for example, chemical synthesis, DNA replication, restriction endonuclease digestion of plasmids or phage DNA, reverse transcription, PCR, or a combination thereof. The oligonucleotide may be modified e.g., by addition of a methyl group, a biotin or digoxigenin moiety, a fluorescent tag or by using radioactive nucleotides.

As used herein, the term "primer" refers to an oligonucleotide, which is capable of acting as a point of initiation of nucleic acid sequence synthesis when placed under conditions in which synthesis of a primer extension product which is complementary to a target nucleic acid strand is induced, i.e., in the presence of different nucleotide triphosphates and a polymerase in an appropriate buffer ("buffer" includes pH, ionic strength, cofactors etc.) and at a suitable temperature. One or more of the nucleotides of the primer can be modified for instance by addition of a methyl group, a biotin or digoxigenin moiety, a fluorescent tag or by using radioactive nucleotides. A primer sequence need not reflect the exact sequence of the template. For example, a non-complementary nucleotide fragment may be attached to the 5' end of the primer, with the remainder of the primer sequence being substantially complementary to the strand. The term primer as used herein includes all forms of primers that may be synthesized including peptide nucleic acid primers, locked nucleic acid primers, phosphorothioate modified primers, labeled primers, and the like. The term "forward primer" as used herein means a primer that anneals to the anti-sense strand of dsDNA. A "reverse primer" anneals to the sense-strand of dsDNA.

As used herein, "primer pair" refers to a forward and reverse primer pair (i.e., a left and right primer pair) that can be used together to amplify a given region of a nucleic acid of interest.

"Probe" as used herein refers to nucleic acid that interacts with a target nucleic acid via hybridization. A probe may be fully complementary to a target nucleic acid sequence or partially complementary. The level of complementarity will depend on many factors based, in general, on the function of the probe. A probe or probes can be used, for example to detect the presence or absence of a mutation in a nucleic acid sequence by virtue of the sequence characteristics of the target. Probes can be labeled or unlabeled, or modified in any of a number of ways well known in the art. A probe may specifically hybridize to a target nucleic acid. Probes may be DNA, RNA or a RNA/DNA hybrid. Probes may be oligonucleotides, artificial chromosomes, fragmented artificial chromosome, genomic nucleic acid, fragmented genomic nucleic acid, RNA, recombinant nucleic acid, fragmented recombinant nucleic acid, peptide nucleic acid (PNA), locked nucleic acid, oligomer of cyclic heterocycles, or conjugates of nucleic acid. Probes may comprise modified nucleobases, modified sugar moieties, and modified internucleotide linkages. A probe may be used to detect the presence or absence of a target nucleic acid. Probes are typically at least about 10, 15, 20, 25, 30, 35, 40, 50, 60, 75, 100 nucleotides or more in length.

As used herein, a "sample" refers to a substance that is being assayed for the presence of a mutation in a nucleic acid of interest. Processing methods to release or otherwise make available a nucleic acid for detection are well known in the art and may include steps of nucleic acid manipulation. A biological sample may be a body fluid or a tissue sample. In some cases, a biological sample may consist of or comprise blood, plasma, sera, urine, feces, epidermal sample, vaginal sample, skin sample, cheek swab, sperm, amniotic fluid, cultured cells, bone marrow sample, tumor biopsies, aspirate and/or chorionic villi, cultured cells, and the like. Fresh, fixed or frozen tissues may also be used. In one embodiment, the sample is preserved as a frozen sample or as formaldehyde- or paraformaldehyde-fixed paraffin-embedded (FFPE) tissue preparation. For example, the sample can be embedded in a matrix, e.g., an FFPE block or a frozen sample. Whole blood samples of about 0.5 to 5 ml collected with EDTA, ACD or heparin as anti-coagulant are suitable.

The term "sensitivity," as used herein in reference to the methods of the present technology, is a measure of the ability of a method to detect a preselected sequence variant in a heterogeneous population of sequences. A method has a sensitivity of S % for variants of F % if, given a sample in which the preselected sequence variant is present as at least F % of the sequences in the sample, the method can detect the preselected sequence at a preselected confidence of C %, S % of the time. By way of example, a method has a sensitivity of 90% for variants of 5% if, given a sample in which the preselected variant sequence is present as at least 5% of the sequences in the sample, the method can detect the preselected sequence at a preselected confidence of 99%, 9 out of 10 times (F=5%; C=99%; S=90%).

The term "specific" as used herein in reference to an oligonucleotide primer means that the nucleotide sequence of the primer has at least 12 bases of sequence identity with a portion of the nucleic acid to be amplified when the oligonucleotide and the nucleic acid are aligned. An oligonucleotide primer that is specific for a nucleic acid is one that, under the stringent hybridization or washing conditions, is capable of hybridizing to the target of interest and not substantially hybridizing to nucleic acids which are not of interest. Higher levels of sequence identity are preferred and include at least 75%, at least 80%, at least 85%, at least 90%, at least 95% and more preferably at least 98% sequence identity.

"Specificity," as used herein, is a measure of the ability of a method to distinguish a truly occurring preselected sequence variant from sequencing artifacts or other closely related sequences. It is the ability to avoid false positive detections. False positive detections can arise from errors introduced into the sequence of interest during sample preparation, sequencing error, or inadvertent sequencing of closely related sequences like pseudo-genes or members of a gene family. A method has a specificity of X % if, when applied to a sample set of $N_{Total}$ sequences, in which $X_{True}$ sequences are truly variant and $X_{Not}$ true are not truly variant, the method selects at least X % of the not truly variant as not variant. E.g., a method has a specificity of 90% if, when applied to a sample set of 1,000 sequences, in which 500 sequences are truly variant and 500 are not truly variant, the method selects 90% of the 500 not truly variant sequences as not variant. Exemplary specificities include 90, 95, 98, and 99%.

The term "stringent hybridization conditions" as used herein refers to hybridization conditions at least as stringent as the following: hybridization in 50% formamide, 5×SSC, 50 mM $NaH_2PO_4$, pH 6.8, 0.5% SDS, 0.1 mg/mL sonicated salmon sperm DNA, and 5× Denhart's solution at 42° C. overnight; washing with 2×SSC, 0.1% SDS at 45° C.; and washing with 0.2×SSC, 0.1% SDS at 45° C. In another example, stringent hybridization conditions should not allow for hybridization of two nucleic acids which differ over a stretch of 20 contiguous nucleotides by more than two bases.

As used herein, the terms "target sequence" and "target nucleic acid sequence" refer to a specific nucleic acid sequence to be detected and/or quantified in the sample to be analyzed.

As used herein, the terms "treat," "treating" or "treatment" refer, to an action to obtain a beneficial or desired clinical result including, but not limited to, alleviation or amelioration of one or more signs or symptoms of a disease or condition (e.g., regression, partial or complete), diminishing the extent of disease, stability (i.e., not worsening, achieving stable disease) state of disease, amelioration or palliation of the disease state, diminishing rate of or time to progression, and remission (whether partial or total).

Intracranial Neoplasms

Craniopharyngiomas are epithelial tumors that typically arise in the suprasellar region of the brain. Craniopharyngiomas occur at an average age-adjusted incidence rate of 0.18 per 100,000. There are two main subtypes of craniopharyngiomas—the adamantinomatous form that is more common in children and the papillary form that occurs predominantly in adults. Located in or above the sella turcica, craniopharyngiomas grow adjacent to the optic chiasm and often extend to involve the hypothalamus, cranial nerves, ventricular system, visual pathways and major blood vessels at the base of the brain. Curative surgery is exceedingly difficult, and resection can contribute to complications. The spectrum of complications include visual defects, severe headaches, pan-hypopituitarism, impaired intellectual function and wide-ranging hypothalamic dysfunction leading to sleep disorders, abnormal thermoregulation and diabetes insipidus, as well as hyperphagia and uncontrollable obesity.

Meningiomas arise from the arachnoidal cap cells of the leptomeninges and constitute approximately one-third of primary central nervous system (CNS) tumors. Most meningiomas (80%) are World Health Organization (WHO) grade I and are treated by surgical resection. However, resection of some meningiomas, particularly at the skull base, is associated with high morbidity. Moreover, 18% of these tumors recur within 5 years, and patients with grade I tumors have significantly reduced long-term survival that is related to both tumor recurrence and stroke risk. Radiation is frequently used as an adjunct to surgery; however, there are no effective chemotherapeutic options when surgery and radiation fail to offer durable long-term disease control. The tumor suppressor NF2 is disrupted in approximately half of all meningiomas, but the complete spectrum of genetic changes remains undefined.

Pituitary adenomas represent 8% of central nervous system tumors. The prevalence of these tumors has been estimated to be 14-22% by autopsy and radiological studies, but clinically significant adenomas occur less frequently, with a prevalence of 68-94 per 100,000 in the general population. These tumors can lead to clinical complications via hormone overproduction or deficiency and/or effects resulting from the mass of the tumor. Prolactinomas (also known as prolactin-secreting pituitary adenomas) are the most frequent subtype, representing 44-66% of all pituitary adenomas. After nonfunctional pituitary adenomas (NFPAs), growth-hormone (GH)-secreting adenomas are the third most frequent subtype, with a prevalence of 8.6 per 100,000 in the general population and an incidence of 3-4 cases per million in the general population per year. The mechanisms underlying pituitary tumorigenesis are unknown. Germline mutations in AIP (encoding aryl-hydrocarbon receptor-interacting protein) and MEN1 (encoding menin) are sometimes found in a few patients with sporadic pituitary adenomas.

Methods for Detecting Polynucleotides Associated with Intracranial Neoplasms

Polynucleotides associated with intracranial neoplasms may be detected by a variety of methods known in the art. Non-limiting examples of detection methods are described below. The detection assays in the methods of the present technology may include purified or isolated DNA (genomic or cDNA), RNA or protein or the detection step may be performed directly from a biological sample without the need for further DNA, RNA or protein purification/isolation.

Nucleic Acid Amplification and/or Detection

Polynucleotides associated with intracranial neoplasms can be detected by the use of nucleic acid amplification techniques that are well known in the art. The starting material may be genomic DNA, cDNA, RNA or mRNA. Nucleic acid amplification can be linear or exponential. Specific variants or mutations may be detected by the use of amplification methods with the aid of oligonucleotide primers or probes designed to interact with or hybridize to a particular target sequence in a specific manner, thus amplifying only the target variant.

Non-limiting examples of nucleic acid amplification techniques include polymerase chain reaction (PCR), reverse transcriptase polymerase chain reaction (RT-PCR), nested PCR, ligase chain reaction (see Abravaya, K. et al., *Nucleic Acids Res*. (1995), 23:675-682), branched DNA signal amplification (see Urdea, M. S. et al., *AIDS* (1993), 7(suppl 2):S11-S14), amplifiable RNA reporters, Q-beta replication, transcription-based amplification, boomerang DNA amplification, strand displacement activation, cycling probe technology, isothermal nucleic acid sequence based amplification (NASBA) (see Kievits, T. et al., *J Virological Methods* (1991), 35:273-286), Invader Technology, next-generation sequencing technology or other sequence replication assays or signal amplification assays.

Primers:

Oligonucleotide primers for use in amplification methods can be designed according to general guidance well known in the art as described herein, as well as with specific requirements as described herein for each step of the particular methods described. In some embodiments, oligonucleotide primers for cDNA synthesis and PCR are 10 to 100 nucleotides in length, preferably between about 15 and about 60 nucleotides in length, more preferably 25 and about 50 nucleotides in length, and most preferably between about 25 and about 40 nucleotides in length.

$T_m$ of a polynucleotide affects its hybridization to another polynucleotide (e.g., the annealing of an oligonucleotide primer to a template polynucleotide). In certain embodiments of the disclosed methods, the oligonucleotide primer used in various steps selectively hybridizes to a target template or polynucleotides derived from the target template (i.e., first and second strand cDNAs and amplified products). Typically, selective hybridization occurs when two polynucleotide sequences are substantially complementary (at least about 65% complementary over a stretch of at least 14 to 25 nucleotides, preferably at least about 75%, more preferably at least about 90% complementary). See Kanehisa, M., *Polynucleotides Res*. (1984), 12:203, incorporated herein by reference. As a result, it is expected that a certain degree of mismatch at the priming site is tolerated. Such mismatch may be small, such as a mono-, di- or tri-nucleotide. In certain embodiments, 100% complementarity exists.

Probes:

Probes are capable of hybridizing to at least a portion of the nucleic acid of interest or a reference nucleic acid (i.e., wild-type sequence). Probes may be an oligonucleotide, artificial chromosome, fragmented artificial chromosome, genomic nucleic acid, fragmented genomic nucleic acid, RNA, recombinant nucleic acid, fragmented recombinant nucleic acid, peptide nucleic acid (PNA), locked nucleic acid, oligomer of cyclic heterocycles, or conjugates of nucleic acid. Probes may be used for detecting and/or capturing/purifying a nucleic acid of interest.

Typically, probes can be about 10 nucleotides, about 20 nucleotides, about 25 nucleotides, about 30 nucleotides, about 35 nucleotides, about 40 nucleotides, about 50 nucleotides, about 60 nucleotides, about 75 nucleotides, or about 100 nucleotides long. However, longer probes are possible. Longer probes can be about 200 nucleotides, about 300 nucleotides, about 400 nucleotides, about 500 nucleotides, about 750 nucleotides, about 1,000 nucleotides, about 1,500 nucleotides, about 2,000 nucleotides, about 2,500 nucleotides, about 3,000 nucleotides, about 3,500 nucleotides, about 4,000 nucleotides, about 5,000 nucleotides, about 7,500 nucleotides, or about 10,000 nucleotides long.

Probes may also include a detectable label or a plurality of detectable labels. The detectable label associated with the probe can generate a detectable signal directly. Additionally, the detectable label associated with the probe can be detected indirectly using a reagent, wherein the reagent includes a detectable label, and binds to the label associated with the probe.

In some embodiments, detectably labeled probes can be used in hybridization assays including, but not limited to Northern blots, Southern blots, microarray, dot or slot blots, and in situ hybridization assays such as fluorescent in situ hybridization (FISH) to detect a target nucleic acid sequence within a biological sample. Certain embodiments may employ hybridization methods for measuring expression of a polynucleotide gene product, such as mRNA. Methods for conducting polynucleotide hybridization assays have been well developed in the art. Hybridization assay procedures and conditions will vary depending on the application and are selected in accordance with the general binding methods known including those referred to in: Maniatis et al. *Molecular Cloning: A Laboratory Manual* (2nd Ed. Cold Spring Harbor, N.Y., 1989); Berger and Kimmel *Methods in Enzymology*, Vol. 152, Guide to Molecular Cloning Techniques (Academic Press, Inc., San Diego, Calif., 1987); Young and Davis, *PNAS*. 80: 1194 (1983).

Detectably labeled probes can also be used to monitor the amplification of a target nucleic acid sequence. In some embodiments, detectably labeled probes present in an amplification reaction are suitable for monitoring the amount of amplicon(s) produced as a function of time. Examples of such probes include, but are not limited to, the 5'-exonuclease assay (TAQMAN® probes described herein (see also U.S. Pat. No. 5,538,848) various stem-loop molecular beacons (see for example, U.S. Pat. Nos. 6,103,476 and 5,925,517 and Tyagi and Kramer, 1996, *Nature Biotechnology* 14:303-308), stemless or linear beacons (see, e.g., WO 99/21881), PNA Molecular Beacons™ (see, e.g., U.S. Pat. Nos. 6,355,421 and 6,593,091), linear PNA beacons (see, for example, Kubista et al., 2001, *SPIE* 4264:53-58), non-FRET probes (see, for example, U.S. Pat. No. 6,150,097), Sunrise®/Amplifluor™ probes (U.S. Pat. No. 6,548,250), stem-loop and duplex Scorpion probes (Solinas et al., 2001, *Nucleic Acids Research* 29:E96 and U.S. Pat. No. 6,589,743), bulge loop probes (U.S. Pat. No. 6,590,091), pseudo knot probes (U.S. Pat. No. 6,589,250), cyclicons (U.S. Pat. No. 6,383,752), MGB Eclipse™ probe (Epoch Biosciences), hairpin probes (U.S. Pat. No. 6,596,490), peptide nucleic acid (PNA) light-up probes, self-assembled nanoparticle probes, and ferrocene-modified probes described, for example, in U.S. Pat. No. 6,485,901; Mhlanga et al., 2001, *Methods* 25:463-471; Whitcombe et al., 1999, *Nature Biotechnology*. 17:804-807; Isacsson et al., 2000, *Molecular*

Cell Probes. 14:321-328; Svanvik et al., 2000, *Anal Biochem.* 281:26-35; Wolffs et al., 2001, *Biotechniques* 766:769-771; Tsourkas et al., 2002, *Nucleic Acids Research.* 30:4208-4215; Riccelli et al., 2002, *Nucleic Acids Research* 30:4088-4093; Zhang et al., 2002 *Shanghai.* 34:329-332; Maxwell et al., 2002, *J. Am. Chem. Soc.* 124:9606-9612; Broude et al., 2002, *Trends Biotechnol.* 20:249-56; Huang et al., 2002, *Chem. Res. Toxicol.* 15:118-126; and Yu et al., 2001, *J. Am. Chem. Soc* 14:11155-11161.

In some embodiments, the detectable label is a fluorophore. Suitable fluorescent moieties include but are not limited to the following fluorophores working individually or in combination: 4-acetamido-4'-isothiocyanatostilbene-2, 2'disulfonic acid; acridine and derivatives: acridine, acridine isothiocyanate; Alexa Fluors: Alexa Fluor® 350, Alexa Fluor® 488, Alexa Fluor® 546, Alexa Fluor® 555, Alexa Fluor® 568, Alexa Fluor® 594, Alexa Fluor® 647 (Molecular Probes); 5-(2-aminoethyl)aminonaphthalene-1-sulfonic acid (EDANS); 4-amino-N-[3-vinylsulfonyl)phenyl]naphthalimide-3,5 disulfonate (Lucifer Yellow VS); N-(4-anilino-1-naphthyl)maleimide; anthranilamide; Black Hole Quencher™ (BHQ™) dyes (biosearch Technologies); BODIPY dyes: BODIPY® R-6G, BOPIPY® 530/550, BODIPY® FL; Brilliant Yellow; coumarin and derivatives: coumarin, 7-amino-4-methylcoumarin (AMC, Coumarin 120), 7-amino-4-trifluoromethylcouluarin (Coumarin 151); Cy2®, Cy3®, Cy3.5®, Cy5®, Cy5.5®; cyanosine; 4',6-diaminidino-2-phenylindole (DAPI); 5',5"-dibromopyrogallol-sulfonephthalein (Bromopyrogallol Red); 7-diethylamino-3-(4'-isothiocyanatophenyl)-4-methylcoumarin; diethylenetriamine pentaacetate; 4,4'-diisothiocyanatodihydro-stilbene-2,2'-disulfonic acid; 4,4'-diisothiocyanatostilbene-2,2'-disulfonic acid; 5-[dimethylamino]naphthalene-1-sulfonyl chloride (DNS, dansyl chloride); 4-(4'-dimethylaminophenylazo)benzoic acid (DABCYL); 4-dimethyl aminophenylazophenyl-4'-isothiocyanate (DABITC); Eclipse™ (Epoch Biosciences Inc.); eosin and derivatives: eosin, eosin isothiocyanate; erythrosin and derivatives: erythrosin B, erythrosin isothiocyanate; ethidium; fluorescein and derivatives: 5-carboxyfluorescein (FAM), 5-(4,6-dichlorotriazin-2-yl)amino fluorescein (DTAF), 2',7'-dimethoxy-4'5'-dichloro-6-carboxyfluorescein (JOE), fluorescein, fluorescein isothiocyanate (FITC), hexachloro-6-carboxyfluorescein (HEX), QFITC (XRITC), tetrachlorofluorescem (TET); fiuorescamine; IR144; IR1446; lanthamide phosphors; Malachite Green isothiocyanate; 4-methylumbelliferone; ortho cresolphthalein; nitrotyrosine; pararosaniline; Phenol Red; B-phycoerythrin, R-phycoerythrin; allophycocyanin; o-phthaldialdehyde; Oregon Green®; propidium iodide; pyrene and derivatives: pyrene, pyrene butyrate, succinimidyl 1-pyrene butyrate; QSY® 7; QSY® 9; QSY® 21; QSY® 35 (Molecular Probes); Reactive Red 4 (Cibacron®Brilliant Red 3B-A); rhodamine and derivatives: 6-carboxy-X-rhodamine (ROX), 6-carboxyrhodamine (R6G), lissamine rhodamine B sulfonyl chloride, rhodamine (Rhod), rhodamine B, rhodamine 123, rhodamine green, rhodamine X isothiocyanate, riboflavin, rosolic acid, sulforhodamine B, sulforhodamine 101, sulfonyl chloride derivative of sulforhodamine 101 (Texas Red); terbium chelate derivatives; N,N,N',N'-tetramethyl-6-carboxyrhodamine (TAMRA); tetramethyl rhodamine; tetramethyl rhodamine isothiocyanate (TRITC); and VIC®. Detector probes can also comprise sulfonate derivatives of fluorescenin dyes with S03 instead of the carboxylate group, phosphoramidite forms of fluorescein, phosphoramidite forms of CY 5 (commercially available for example from Amersham).

Detectably labeled probes can also include quenchers, including without limitation black hole quenchers (Biosearch), Iowa Black (IDT), QSY quencher (Molecular Probes), and Dabsyl and Dabcel sulfonate/carboxylate Quenchers (Epoch).

Detectably labeled probes can also include two probes, wherein for example a fluorophore is on one probe, and a quencher is on the other probe, wherein hybridization of the two probes together on a target quenches the signal, or wherein hybridization on the target alters the signal signature via a change in fluorescence.

In some embodiments, interchelating labels such as ethidium bromide, SYBR® Green I (Molecular Probes), and PicoGreen® (Molecular Probes) are used, thereby allowing visualization in real-time, or at the end point, of an amplification product in the absence of a detector probe. In some embodiments, real-time visualization may involve the use of both an intercalating detector probe and a sequence-based detector probe. In some embodiments, the detector probe is at least partially quenched when not hybridized to a complementary sequence in the amplification reaction, and is at least partially unquenched when hybridized to a complementary sequence in the amplification reaction.

In some embodiments, the amount of probe that gives a fluorescent signal in response to an excited light typically relates to the amount of nucleic acid produced in the amplification reaction. Thus, in some embodiments, the amount of fluorescent signal is related to the amount of product created in the amplification reaction. In such embodiments, one can therefore measure the amount of amplification product by measuring the intensity of the fluorescent signal from the fluorescent indicator.

Primers or probes can be designed so that they hybridize under stringent conditions to the allelic variants of BRAF, PIK3R2, CNTNAP1, CTNNB1, SLIT1, NTRK3, HUWE1, CASKIN1, JMJD7, OR51T1, FAM20A, INHBA, OGDH, EPN3, LYPD2, SF3B1, APOD, CATSPER3, SEC16A, OR5T3, TANK, TAS1R3, RBPJL, ADAMTS16, PTAR1, PCDH20, BRCA2, WDR45, ATG4B, ZNF407, H6PD, NF2, BBS12, PSMD12, or TNN but not to the respective wild-type nucleotide sequences. Primers or probes can also be prepared that are complementary and specific for the wild-type nucleotide sequence of BRAF, PIK3R2, CNTNAP1, CTNNB1, SLIT1, NTRK3, HUWE1, CASKIN1, JMJD7, OR51T1, FAM20A, INHBA, OGDH, EPN3, LYPD2, SF3B1, APOD, CATSPER3, SEC16A, OR5T3, TANK, TAS1R3, RBPJL, ADAMTS16, PTAR1, PCDH20, BRCA2, WDR45, ATG4B, ZNF407, H6PD, NF2, BBS12, PSMD12, or TNN but not to any one of the corresponding allelic variants described herein.

In some embodiments, detection can occur through any of a variety of mobility dependent analytical techniques based on the differential rates of migration between different nucleic acid sequences. Exemplary mobility-dependent analysis techniques include electrophoresis, chromatography, mass spectroscopy, sedimentation, for example, gradient centrifugation, field-flow fractionation, multi-stage extraction techniques, and the like. In some embodiments, mobility probes can be hybridized to amplification products, and the identity of the target nucleic acid sequence determined via a mobility dependent analysis technique of the eluted mobility probes, as described in Published PCT Applications WO04/46344 and WO01/92579. In some embodiments, detection can be achieved by various microarrays and related software such as the Applied Biosystems Array System with the Applied Biosystems 1700 Chemiluminescent Microarray Analyzer and other commercially available array systems available from Affymetrix, Agilent, Illumina, and Amersham Biosciences, among others (see also Gerry et al., *J. Mol. Biol.* 292:251-62, 1999; De Bellis et al., *Minerva Biotec* 14:247-52, 2002; and Stears et al., *Nat. Med.* 9:14045, including supplements, 2003).

It is also understood that detection can comprise reporter groups that are incorporated into the reaction products, either as part of labeled primers or due to the incorporation of labeled dNTPs during an amplification, or attached to reaction products, for example but not limited to, via hybridization tag complements comprising reporter groups or via linker arms that are integral or attached to reaction products. In some embodiments, unlabeled reaction products may be detected using mass spectrometry.

NGS Platforms

In some embodiments, high throughput, massively parallel sequencing employs sequencing-by-synthesis with reversible dye terminators. In other embodiments, sequencing is performed via sequencing-by-ligation. In yet other embodiments, sequencing is single molecule sequencing. Examples of Next Generation Sequencing techniques include, but are not limited to pyrosequencing, Reversible dye-terminator sequencing, SOLiD sequencing, Ion semiconductor sequencing, Helioscope single molecule sequencing etc.

The Ion Torrent™ (Life Technologies, Carlsbad, CA) amplicon sequencing system employs a flow-based approach that detects pH changes caused by the release of hydrogen ions during incorporation of unmodified nucleotides in DNA replication. For use with this system, a sequencing library is initially produced by generating DNA fragments flanked by sequencing adapters. In some embodiments, these fragments can be clonally amplified on particles by emulsion PCR. The particles with the amplified template are then placed in a silicon semiconductor sequencing chip. During replication, the chip is flooded with one nucleotide after another, and if a nucleotide complements the DNA molecule in a particular microwell of the chip, then it will be incorporated. A proton is naturally released when a nucleotide is incorporated by the polymerase in the DNA molecule, resulting in a detectable local change of pH. The pH of the solution then changes in that well and is detected by the ion sensor. If homopolymer repeats are present in the template sequence, multiple nucleotides will be incorporated in a single cycle. This leads to a corresponding number of released hydrogens and a proportionally higher electronic signal.

The 454TM GS FLX™ sequencing system (Roche, Germany), employs a light-based detection methodology in a large-scale parallel pyrosequencing system. Pyrosequencing uses DNA polymerization, adding one nucleotide species at a time and detecting and quantifying the number of nucleotides added to a given location through the light emitted by the release of attached pyrophosphates. For use with the 454™ system, adapter-ligated DNA fragments are fixed to small DNA-capture beads in a water-in-oil emulsion and amplified by PCR (emulsion PCR). Each DNA-bound bead is placed into a well on a picotiter plate and sequencing reagents are delivered across the wells of the plate. The four DNA nucleotides are added sequentially in a fixed order across the picotiter plate device during a sequencing run. During the nucleotide flow, millions of copies of DNA bound to each of the beads are sequenced in parallel. When a nucleotide complementary to the template strand is added to a well, the nucleotide is incorporated onto the existing DNA strand, generating a light signal that is recorded by a CCD camera in the instrument.

Sequencing technology based on reversible dye-terminators: DNA molecules are first attached to primers on a slide and amplified so that local clonal colonies are formed. Four types of reversible terminator bases (RT-bases) are added, and non-incorporated nucleotides are washed away. Unlike pyrosequencing, the DNA can only be extended one nucleotide at a time. A camera takes images of the fluorescently labeled nucleotides, then the dye along with the terminal 3' blocker is chemically removed from the DNA, allowing the next cycle.

Helicos's single-molecule sequencing uses DNA fragments with added polyA tail adapters, which are attached to the flow cell surface. At each cycle, DNA polymerase and a single species of fluorescently labeled nucleotide are added, resulting in template-dependent extension of the surface-immobilized primer-template duplexes. The reads are performed by the Helioscope sequencer. After acquisition of images tiling the full array, chemical cleavage and release of the fluorescent label permits the subsequent cycle of extension and imaging.

Sequencing by synthesis (SBS), like the "old style" dye-termination electrophoretic sequencing, relies on incorporation of nucleotides by a DNA polymerase to determine the base sequence. A DNA library with affixed adapters is denatured into single strands and grafted to a flow cell, followed by bridge amplification to form a high-density array of spots onto a glass chip. Reversible terminator methods use reversible versions of dye-terminators, adding one nucleotide at a time, detecting fluorescence at each position by repeated removal of the blocking group to allow polymerization of another nucleotide. The signal of nucleotide incorporation can vary with fluorescently labeled nucleotides, phosphate-driven light reactions and hydrogen ion sensing having all been used. Examples of SBS platforms include Illumina GA and HiSeq 2000. The MiSeq® personal sequencing system (Illumina, Inc.) also employs sequencing by synthesis with reversible terminator chemistry.

In contrast to the sequencing by synthesis method, the sequencing by ligation method uses a DNA ligase to determine the target sequence. This sequencing method relies on enzymatic ligation of oligonucleotides that are adjacent through local complementarity on a template DNA strand. This technology employs a partition of all possible oligonucleotides of a fixed length, labeled according to the sequenced position. Oligonucleotides are annealed and ligated and the preferential ligation by DNA ligase for matching sequences results in a dinucleotide encoded color space signal at that position (through the release of a fluorescently labeled probe that corresponds to a known nucleotide at a known position along the oligo). This method is primarily used by Life Technologies' SOLiD™ sequencers. Before sequencing, the DNA is amplified by emulsion PCR. The resulting beads, each containing only copies of the same DNA molecule, are deposited on a solid planar substrate.

SMRT™ sequencing is based on the sequencing by synthesis approach. The DNA is synthesized in zero-mode wave-guides (ZMWs)-small well-like containers with the capturing tools located at the bottom of the well. The sequencing is performed with use of unmodified polymerase (attached to the ZMW bottom) and fluorescently labeled nucleotides flowing freely in the solution. The wells are constructed in a way that only the fluorescence occurring at the bottom of the well is detected. The fluorescent label is detached from the nucleotide at its incorporation into the DNA strand, leaving an unmodified DNA strand.

Intracranial Neoplasm Screening Methods of the Present Technology

Disclosed herein are methods and assays that are based on the principle that assaying cell populations within an intracranial tumor sample for the presence of one or more alterations in BRAF, PIK3R2, CNTNAP1, CTNNB1, SLIT1, NTRK3, HUWE1, CASKIN1, JMJD7, OR51T1, FAM20A, INHBA, OGDH, EPN3, LYPD2, SF3B1, APOD, CATSPER3, SEC16A, OR5T3, TANK, TAS1R3, RBPJL, ADAMTS16, PTAR1, PCDH20, BRCA2, WDR45, ATG4B, ZNF407, H6PD, NF2, BBS12, PSMD12, and TNN, is useful in determining whether a patient will benefit from or will respond to treatment with an individual therapeutic agent or a specific combination of therapeutic agents.

In some embodiments, the methods disclosed herein rely on high throughput massively parallel sequencing of a large number of diverse genes, e.g., from tumor or control samples. In one embodiment, the methods featured in the present technology are used in a multiplex, multi-gene assay format, e.g., assays that incorporate multiple signals from a large number of diverse genetic alterations in a large number of genes.

The present disclosure provides methods for detecting at least one genetic mutation in an intracranial tumor of a subject comprising (a) extracting DNA from a fresh or frozen intracranial tumor sample obtained from the subject; (b) extracting DNA from a control tissue sample obtained from the subject; (c) generating a first library from the intracranial tumor sample comprising amplicons corresponding to a first plurality of genes; (d) generating a second library from the control tissue sample comprising amplicons corresponding to a second plurality of genes; (e) ligating a first adapter sequence comprising a first barcode sequence to the ends of the amplicons corresponding to the first plurality of genes; (f) ligating a second adapter sequence comprising a second barcode sequence to the ends of the amplicons corresponding to the second plurality of genes; and (g) detecting at least one genetic mutation in the amplicons corresponding to the first plurality of genes using high throughput massive parallel sequencing, wherein the at least one genetic mutation (i) corresponds to at least one gene selected from the group consisting of: PIK3R2, CNTNAP1, SLIT1, NTRK3, HUWE1, CASKIN1, JMJD7, OR51T1, FAM20A, INHBA, OGDH, EPN3, LYPD2, SF3B1, APOD, CATSPER3, SEC16A, OR5T3, TANK, TAS1R3, RBPJL, ADAMTS16, PTAR1, PCDH20, BRCA2, WDR45, ATG4B, ZNF407, H6PD, NF2, BBS12, PSMD12, and TNN; and (ii) is not detected in the amplicons corresponding to the second plurality of genes. In some embodiments, the control tissue sample is a matched whole blood sample from the subject. In some embodiments, the methods of the present technology further comprise detecting a BRAF mutation or a CTNNB1 mutation in the amplicons corresponding to the first plurality of genes, wherein the BRAF mutation or the CTNNB1 mutation is not detected in the amplicons corresponding to the second plurality of genes.

In some embodiments of the method, the at least one genetic mutation detected is PIK3R2 E593K, CNTNAP1 R270Q, SLIT1 H566R, NTRK3 V221I, HUWE1 S2039F, CASKIN1 P1196L, JMJD7 L185F, OR51T1 R329H, FAM20A S119R, INHBA P291S, OGDH I446F, EPN3 D458E, LYPD2 R24C, SF3B1 R625C, APOD D144Y, CATSPER3 E304A, SEC16A G1091R, OR5T3 L144H, TANK R394Q, TAS1R3 D307H, RBPJL L181P, ADAMTS16 P870S, PTAR1 D89A, PCDH20 D773H, BRCA2 P3067L, WDR45 R280C, ATG4B R49G, ZNF407 C120Y, H6PD P725T, NF2 Q324*, BBS12 R431P, PSMD12 I66V, or TNN L278V. In some embodiments, the BRAF mutation is BRAF V600E. In other embodiments, the CTNNB1 mutation is CTNNB1 S37C, CTNNB1 T41I or CTNNB1 S33C.

Additionally or alternatively, in some embodiments of the method, the intracranial tumor is a pituitary adenoma, meningioma, or craniopharyngioma. In certain embodiments, the pituitary adenoma is prolactin-secreting or ACTH-secreting. Additionally or alternatively, in some embodiments, the pituitary adenoma is not associated with a mutation in AIP or MEN1. In some embodiments, the craniopharyngioma is papillary or adamantinomatous.

In some embodiments, a single primer or one or both primers of a primer pair comprise a specific adapter sequence (also referred to as a sequencing adapter) ligated to the 5' end of the target specific sequence portion of the primer. This sequencing adapter is a short oligonucleotide of known sequence that can provide a priming site for both amplification and sequencing of the adjoining, unknown target nucleic acid. As such, adapters allow binding of a fragment to a flow cell for next generation sequencing. Any adapter sequence may be included in a primer used in the present technology. In certain embodiments, amplicons corresponding to specific regions of BRAF, PIK3R2, CNTNAP1, CTNNB1, SLIT1, NTRK3, HUWE1, CASKIN1, JMJD7, OR51T1, FAM20A, INHBA, OGDH, EPN3, LYPD2, SF3B1, APOD, CATSPER3, SEC16A, OR5T3, TANK, TAS1R3, ADAMTS16, PTAR1, PCDH20, BRCA2, WDR45, ATG4B, ZNF407, H6PD, NF2, BBS12, PSMD12, and TNN are amplified using primers that contain an oligonucleotide sequencing adapter to produce adapter tagged amplicons.

In other embodiments, the employed primers do not contain adapter sequences and the amplicons produced are subsequently (i.e. after amplification) ligated to an oligonucleotide sequencing adapter on one or both ends of the amplicons. In some embodiments, all forward amplicons (i.e., amplicons extended from forward primers that hybridized with antisense strands of a target nucleic acid) contain the same adapter sequence. In some embodiments when double stranded sequencing is performed, all forward amplicons contain the same adapter sequence and all reverse amplicons (i.e., amplicons extended from reverse primers that hybridized with sense strands of a target segment) contain an adapter sequence that is different from the adapter sequence of the forward amplicons. In some embodiments, the adapter sequences further comprise an index sequence (also referred to as an index tag, a "barcode" or a multiplex identifier (MID)).

In some embodiments, the adapter sequences are P5 and/or P7 adapter sequences that are recommended for Illumina sequencers (MiSeq and HiSeq). See, e.g., Williams-Carrier et al., Plant 1, 63(1):167-77 (2010). In some embodiments, the adapter sequences are P1, A, or Ion Xpress™ barcode adapter sequences that are recommended for Life Technologies sequencers. Other adapter sequences are known in the art. Some manufacturers recommend specific adapter sequences for use with the particular sequencing technology and machinery that they offer.

Additionally or alternatively, in some embodiments of the above methods, amplicons corresponding to specific regions of BRAF, PIK3R2, CNTNAP1, CTNNB1, SLIT1, NTRK3, HUWE1, CASKIN1, JMJD7, OR51T1, FAM20A, INHBA, OGDH, EPN3, LYPD2, SF3B1, APOD, CATSPER3, SEC16A, OR5T3, TANK, TAS1R3, RBPJL, ADAMTS16, PTAR1, PCDH20, BRCA2, WDR45, ATG4B, ZNF407, H6PD, NF2, BBS12, PSMD12, and TNN from more than one sample are sequenced. In some embodiments, all samples are sequenced simultaneously in parallel.

In some embodiments of the above methods, amplicons corresponding to specific regions of BRAF, PIK3R2, CNTNAP1, CTNNB1, SLIT1, NTRK3, HUWE1, CASKIN1, JMJD7, OR51T1, FAM20A, INHBA, OGDH, EPN3, LYPD2, SF3B1, APOD, CATSPER3, SEC16A, OR5T3, TANK, TAS1R3, RBPJL, ADAMTS16, PTAR1, PCDH20, BRCA2, WDR45, ATG4B, ZNF407, H6PD, NF2, BBS12, PSMD12, and INN from at least 1, 5, 10, 20, 30 or up to 35, 40, 45, 48 or 50 different samples are amplified and sequenced using the methods described herein.

Additionally or alternatively, in some embodiments of the method, amplicons derived from a single sample may further comprise an identical index sequence that indicates the source from which the amplicon is generated, the index sequence for each sample being different from the index sequences from all other samples. As such, the use of index sequences permits multiple samples to be pooled per sequencing run and the sample source subsequently ascertained based on the index sequence. In some embodiments, the Access Array™ System (Fluidigm Corp., San Francisco, CA) or the Apollo 324 System (Wafergen Biosystems, Fremont, CA) is used to generate a barcoded (indexed) amplicon library by simultaneously amplifying the nucleic acids from the samples in one set up.

In some embodiments, indexed amplicons are generated using primers (for example, forward primers and/or reverse primers) containing the index sequence. Such indexed primers may be included during library preparation as a "barcoding" tool to identify specific amplicons as originating from a particular sample source. When adapter-ligated and/or indexed primers are employed, the adapter sequence and/or index sequence gets incorporated into the amplicon (along with the target-specific primer sequence) during amplification. Therefore, the resulting amplicons are sequencing-competent and do not require the traditional library preparation protocol. Moreover, the presence of the index tag permits the differentiation of sequences from multiple sample sources.

In some embodiments, the amplicons may be amplified with non-adapter-ligated and/or non-indexed primers and a sequencing adapter and/or an index sequence may be subsequently ligated to one or both ends of each of the resulting amplicons. In some embodiments, the amplicon library is generated using a multiplexed PCR approach.

Indexed amplicons from more than one sample source are quantified individually and then pooled prior to high throughput sequencing. As such, the use of index sequences permits multiple samples (i.e., samples from more than one sample source) to be pooled per sequencing run and the sample source subsequently ascertained based on the index sequence. "Multiplexing" is the pooling of multiple adapter-tagged and indexed libraries into a single sequencing run. When indexed primer sets are used, this capability can be exploited for comparative studies. In some embodiments, amplicon libraries from up to 48 separate sources are pooled prior to sequencing.

Following the production of an adapter tagged and, optionally indexed, amplicon library, the amplicons are sequenced using high throughput, massively parallel sequencing (i.e., next generation sequencing). Methods for performing high throughput, massively parallel sequencing are known in the art. In some embodiments of the method, the high throughput massive parallel sequencing is performed using 454TM GS FLX™ pyrosequencing, reversible dye-terminator sequencing, SOLiD sequencing, ION semiconductor sequencing, Helioscope single molecule sequencing, sequencing by synthesis, sequencing by ligation, or SMRT™ sequencing. In some embodiments, high throughput massively parallel sequencing may be performed using a read depth approach.

In one aspect, the present disclosure provides a method of detecting the presence of at least one actionable genetic mutation in an intracranial tumor of a subject comprising (a) contacting a nucleic acid obtained from an intracranial tumor sample with at least one primer pair that amplifies at least one gene selected from PIK3R2, CNTNAP1, SLIT1, NTRK3, HUWE1, CASKIN1, JMJD7, OR51T1, FAM20A, INHBA, OGDH, EPN3, LYPD2, SF3B1, APOD, CATSPER3, SEC16A, OR5T3, TANK, TAS1R3, RBPJL, ADAMTS16, PTAR1, PCDH20, BRCA2, WDR45, ATG4B, ZNF407, H6PD, NF2, BBS12, PSMD12, and TNN; and (b) detecting at least one allelic variant in the nucleic acid, wherein the at least one allelic variant is selected from the group consisting of PIK3R2 E593K, CNTNAP1 R270Q, SLIT1 H566R, NTRK3 V221I, HUWE1 S2039F, CASKIN1 P1196L, JMJD7 L185F, OR51T1 R329H, FAM20A S119R, INHBA P291S, OGDH I446F, EPN3 D458E, LYPD2 R24C, SF3B1 R625C, APOD D144Y, CATSPER3 E304A, SEC16A G1091R, OR5T3 L144H, TANK R394Q, TAS1R3 D307H, RBPJL L181P, ADAMTS16 P870S, PTAR1 D89A, PCDH20 D773H, BRCA2 P3067L, WDR45 R280C, ATG4B R49G, ZNF407 C120Y, H6PD P725T, NF2 Q324*, BBS12 R431P, PSMD12 I66V, and TNN L278V, wherein detecting the at least one allelic variant is indicative of the presence of an actionable genetic mutation in the intracranial tumor of the subject.

In another aspect, the present disclosure provides a method of detecting the presence of at least one actionable genetic mutation in an intracranial tumor of a subject comprising (a) contacting a nucleic acid obtained from an intracranial tumor sample with one or more probes that hybridize to at least one gene selected from PIK3R2, CNTNAP1, SLIT1, NTRK3, HUWE1, CASKIN1, JMJD7, OR51T1, FAM20A, INHBA, OGDH, EPN3, LYPD2, SF3B1, APOD, CATSPER3, SEC16A, OR5T3, TANK, TAS1R3, RBPJL, ADAMTS16, PTAR1, PCDH20, BRCA2, WDR45, ATG4B, ZNF407, H6PD, NF2, BBS12, PSMD12, and TNN; wherein the one or more probes can recognize and discriminate allelic variants of PIK3R2, CNTNAP1, SLIT NTRK3, HUWE1, CASKIN1, JMJD7, OR51T1, FAM20A, INHBA, OGDH, EPN3, LYPD2, SF3B1, APOD, CATSPER3, SEC16A, OR5T3, TANK, TAS1R3, RBPJL, ADAMTS16, PTAR1, PCDH20, BRCA2, WDR45, ATG4B, ZNF407, H6PD, NF2, BBS12, PSMD12, and TNN; and (b) detecting at least one allelic variant in the nucleic acid, wherein the at least one allelic variant is selected from the group consisting of BRAF V600E, CTNNB1 S37C, CTNNB1 T41I, CTNNB1 S33C, PIK3R2 E593K, CNTNAP1 R270Q, SLIT1 H566R, NTRK3 V221I, HUWE1 S2039F, CASKIN1 P1196L, JMJD7 L185F, OR51T1 R329H, FAM20A S119R, INHBA P291S, OGDH I446F, EPN3 D458E, LYPD2 R24C, SF3B1 R625C, APOD D144Y, CATSPER3 E304A, SEC16A G1091R, OR5T3 L144H, TANK R394Q, TAS1R3 D307H, RBPJL L181P, ADAMTS16 P870S, PTAR1 D89A, PCDH20 D773H, BRCA2 P3067L, WDR45 R280C, ATG4B R49G, ZNF407 C120Y, H6PD P725T, NF2 Q324*, BBS12 R431P, PSMD12 I66V, and TNN L278V, wherein detecting the at least one allelic variant is indicative of the presence of an actionable genetic mutation in the intracranial tumor of the subject.

Treatment of Intracranial Neoplasms

Disclosed herein are methods for determining whether a patient with an intracranial neoplasm, such as a pituitary adenoma, meningioma, or craniopharyngioma, will benefit from or is predicted to be responsive to treatment with an individual therapeutic agent or a specific combination of therapeutic agents.

In one aspect, the present disclosure provides a method for selecting a subject with an intracranial neoplasm for treatment with one or more chemotherapeutic agents comprising (a) extracting DNA from a fresh or frozen intracranial tumor sample obtained from the subject; (b) generating a DNA library from the intracranial tumor sample, wherein the DNA library comprises amplicons corresponding to a plurality of genes; (c) detecting at least one genetic mutation in at least one of the amplicons; and (d) selecting the subject for treatment with one or more chemotherapeutic agents, if a mutation in at least one of the amplicons corresponding to at least one gene selected from PIK3R2, CNTNAP1, SLIT1, NTRK3, HUWE1, CASKIN1, JMJD7, OR51T1, FAM20A, INHBA, OGDH, EPN3, LYPD2, SF3B1, APOD, CATSPER3, SEC16A, OR5T3, TANK, TAS1R3, RBPJL, ADAMTS16, PTAR1, PCDH20, BRCA2, WDR45, ATG4B, ZNF407, H6PD, NF2, BBS12, PSMD12, and TNN is detected.

In another aspect, the present disclosure provides a method for treating an intracranial neoplasm in a subject in need thereof comprising administering a therapeutically effective amount of one or more chemotherapeutic agents to the subject, wherein the subject harbors a mutation in the coding region of one or more genes selected from the group consisting of PIK3R2, CNTNAP1, SLIT1, NTRK3, HUWE1, CASKIN1, JMJD7, OR51T1, FAM20A, INHBA, OGDH, EPN3, LYPD2, SF3B1, APOD, CATSPER3, SEC16A, OR5T3, TANK, TAS1R3, RBPJL, ADAMTS16, PTAR1, PCDH20, BRCA2, WDR45, ATG4B, ZNF407, H6PD, NF2, BBS12, PSMD12, and TNN.

In any of the above embodiments, the subject harbors an additional mutation selected from the group consisting of BRAF V600E, CTNNB1 S37C, CTNNB1 T41I and CTNNB1 S33C. Additionally or alternatively, in any of the above embodiments, the subject harbors one or mutations selected from the group consisting of PIK3R2 E593K, CNTNAP1 R270Q, SLIT1 H566R, NTRK3 V221I, HUWE1 S2039F, CASKIN1 P1196L, JMJD7 L185F, OR51T1 R329H, FAM20A S119R, INHBA P291S, OGDH I446F, EPN3 D458E, LYPD2 R24C, SF3B1 R625C, APOD D144Y, CATSPER3 E304A, SEC16A G1091R, OR5T3 L144H, TANK R394Q, TAS1R3 D307H, RBPJL L181P, ADAMTS16 P870S, PTAR1 D89A, PCDH20 D773H, BRCA2 P3067L, WDR45 R280C, ATG4B R49G, ZNF407 C120Y, H6PD P725T, NF2 Q324*, BBS12 R431P, PSMD12 I66V, and TNN L278V.

In some embodiments of the methods of the present technology, the intracranial neoplasm is a pituitary adenoma, meningioma, or craniopharyngioma. In certain embodiments, the pituitary adenoma is prolactin-secreting or ACTH-secreting. Additionally or alternatively, in some embodiments, the pituitary adenoma is not associated with a mutation in AIP or MEN1. In some embodiments, the craniopharyngioma is papillary or adamantinomatous.

In some embodiments, the chemotherapeutic agent(s) comprise one or more of BRAF inhibitors, SF3b complex inhibitors, dopamine agonists, pasireotide (Signifor®), cyproheptadine (Periactin®), steroidogenesis inhibitors, Mifepristone (Korlym®), PI3K/AKT/mTOR pathway inhibitors, GnRH antagonists, WNT signaling pathway inhibitors, and other therapeutic drugs useful for treating brain neoplasms.

Examples of BRAF inhibitors include, but are not limited to GDC-0879, SB590885, Encorafenib, RAF265, TAK-632, PLX4720, CEP-32496, AZ628, Sorafenib Tosylate, Sorafenib, Vemurafenib (Zelboraf) and Dabrafenib (GSK2118436). The BRAF inhibitor vemurafenib is used treat BRAF V600 mutation-positive tumors.

Examples of SF3b complex inhibitors include, but are not limited to spliceostatin A.

Examples of dopamine agonists include, but are not limited to cabergoline and bromocriptine (Parlodel®).

Examples of steroidogenesis inhibitors include, but are not limited to ketoconazole, aminoglutethimide, etomidate, metyrapone, and mitotane.

Examples of PI3K/AKT/mTOR pathway inhibitors include, but are not limited to BKM120, BEZ235, Pictilisib (GDC-0941), LY294002, CAL-101 (Idelalisib), GNE-317, PI-3065, HS-173, PI-103, NU7441, GSK2636771, VS-5584, CZC24832, Duvelisib, TG100-115, A66, YM201636, CAY10505, GSK1059615, PF-04691502, PIK-75, PIK-93, AS-605240, BGT226, AZD6482, Voxtalisib, Alpelisib, CUDC-907, IC-87114, Omipalisib, TG100713, Gedatolisib, CH5132799, PKI-402, BAY 80-6946, TGX-221, XL147, PIK-90, PIK-293, PIK-294, 3-Methyladenine, Quercetin, Wortmannin, ZSTK474, AS-252424, AS-604850, sirolimus (rapamycin), everolimus, AZD2014, and Apitolisib.

Examples of GnRH antagonists include, but are not limited to cetrorelix, ganirelix, abarelix, degarelix, elagolix, relugolix (TAK-385), KLH-2109, and ASP-1707.

Examples of WNT signaling pathway inhibitors include, but are not limited to ICG-001, iCRT3, iCRT5, iCRT14, BC21, NC043 (15-oxospiramilactone), PKF115-584, CGP049090, PKF118-310, Thiazolidinediones (A2TG and STG28), Murrayafoline A, OSU03012, 3,6-dihydroxyflavone, PNU-7465431, CCT036477, CCT070535, CCT031374, and non-steroidal anti-inflammatory drugs (NSAIDs).

Examples of other therapeutic drugs useful for treating brain neoplasms include, but are not limited to temozolomide, procarbazine, carmustine (BCNU), lomustine (CCNU), vincristine, irinotecan, cisplatin, carboplatin, methotrexate, etoposide, bleomycin, vinblastine, actinomycin (Dactinomycin), cyclophosphamide, and ifosfamide. Such therapeutic drugs may be included in the methods described herein.

In one aspect, the present disclosure provides a method for selecting a subject with an intracranial neoplasm for treatment with a PI3K/AKT/mTOR pathway inhibitor and a BRAF inhibitor comprising: (a) extracting DNA from a fresh or frozen intracranial tumor sample obtained from the subject; (b) generating a DNA library from the intracranial tumor sample, wherein the DNA library comprises amplicons corresponding to a plurality of genes; (c) detecting at least one mutation in at least one of the amplicons; and (d) selecting the subject for treatment with a PI3K/AKT/mTOR pathway inhibitor and a BRAF inhibitor, if a mutation in at least one of the amplicons corresponding to PIK3R2 and a mutation in at least one of the amplicons corresponding to BRAF are detected. In some embodiments of the method, the intracranial neoplasm is a craniopharyngioma.

In another aspect, the present disclosure provides a method for treating an intracranial neoplasm in a subject in need thereof comprising administering a therapeutically effective amount of a PI3K/AKT/mTOR pathway inhibitor to the subject, wherein the subject harbors a mutation in the coding region of PIK3R2. In some embodiments, the mutation is PIK3R2 E593K. In some embodiments, the intracranial neoplasm is a craniopharyngioma. Additionally or alternatively, in some embodiments, the method further comprises administering a therapeutically effective amount of a BRAF inhibitor.

In one aspect, the present disclosure provides a method for selecting a subject with an intracranial neoplasm for treatment with a WNT signaling pathway inhibitor and a GnRH antagonist comprising: (a) extracting DNA from a fresh or frozen intracranial tumor sample obtained from the subject; (b) generating a DNA library from the intracranial tumor sample, wherein the DNA library comprises amplicons corresponding to a plurality of genes; (c) detecting at least one mutation in at least one of the amplicons; and (d) selecting the subject for treatment with a WNT signaling pathway inhibitor and a GnRH antagonist, if a mutation in at least one of the amplicons corresponding to CTNNB1 and a mutation in at least one of the amplicons corresponding to INHBA are detected. In some embodiments of the method, the intracranial neoplasm is a craniopharyngioma.

In one aspect, the present disclosure provides a method for treating an intracranial neoplasm in a subject in need thereof comprising administering a therapeutically effective amount of a GnRH antagonist to the subject, wherein the subject harbors a mutation in the coding region of INHBA. In some embodiments, the mutation is INHBA P291S. In some embodiments, the intracranial neoplasm is a craniopharyngioma. Additionally or alternatively, in some embodiments, the method further comprises administering a therapeutically effective amount of a WNT signaling pathway inhibitor.

In another aspect, the present disclosure provides a method for predicting the likelihood of responsiveness of a subject with a pituitary adenoma to treatment with a SF3b complex inhibitor comprising: (a) extracting DNA from a fresh or frozen intracranial tumor sample obtained from the subject; (b) generating a DNA library from the intracranial tumor sample, wherein the DNA library comprises amplicons corresponding to a plurality of genes; (c) detecting at least one mutation in at least one of the amplicons; and (d) identifying the subject as having a high likelihood of responsiveness to treatment with a SF3b complex inhibitor, when a mutation in at least one of the amplicons corresponding to SF3B1 is detected. In some embodiments, the pituitary adenoma is prolactin-secreting or ACTH-secreting. Additionally or alternatively, in some embodiments, the pituitary adenoma is not associated with a mutation in AIP or MEN1.

In one aspect, the present disclosure provides a method for treating an intracranial neoplasm in a subject in need thereof comprising administering a therapeutically effective amount of a SF3b complex inhibitor to the subject, wherein the subject harbors a mutation in the coding region of SF3B1. In some embodiments, the mutation is SF3B1 R625C. Additionally or alternatively, in some embodiments, the intracranial neoplasm is a pituitary adenoma. In a further embodiment, the pituitary adenoma is prolactin-secreting.

Kits

The present disclosure also provides kits for detecting alterations in nucleic acid sequences corresponding to BRAF, PIK3R2, CNTNAP1, CTNNB1, SLIT1, NTRK3, HUWE1, CASKIN1, JMJD7, OR51T1, FAM20A, INHBA, OGDH, EPN3, LYPD2, SF3B1, APOD, CATSPER3, SEC16A, OR5T3, TANK, TAS1R3, RBPJL, ADAMTS16, PTAR1, PCDH20, BRCA2, WDR45, ATG4B, ZNF407, H6PD, NF2, BBS12, PSMD12, and TNN.

Kits of the present technology comprise one or more primer pairs that selectively hybridize and are useful in amplifying one or more of the genes selected from the group consisting of BRAF, PIK3R2, CNTNAP1, CTNNB1, SLIT1, NTRK3, HUWE1, CASKIN1, JMJD7, OR51T1, FAM20A, INHBA, OGDH, EPN3, LYPD2, SF3B1, APOD, CATSPER3, SEC16A, OR5T3, TANK, TAS1R3, RBPJL, ADAMTS16, PTAR1, PCDH20, BRCA2, WDR45, ATG4B, ZNF407, H6PD, NF2, BBS12, PSMD12, and TNN SEC16A, OR5T3, TANK, TAS1R3, RBPJL, ADAMTS16, PTAR1, PCDH20, BRCA2, WDR45, ATG4B, ZNF407, H6PD, NF2, BBS12, PSMD12, and TNN.

In some embodiments, the kits of the present technology comprise a single primer pair that hybridizes to an exon of a single gene selected from the group consisting of BRAF, PIK3R2, CNTNAP1, CTNNB1, SLIT1, NTRK3, HUWE1, CASKIN1, JMJD7, OR51T1, FAM20A, INHBA, OGDH, EPN3, LYPD2, SF3B1, APOD, CATSPER3, SEC16A, OR5T3, TANK, TAS1R3, RBPJL, ADAMTS16, PTAR1, PCDH20, BRCA2, WDR45, ATG4B, ZNF407, H6PD, NF2, BBS12, PSMD12, and TNN.

In other embodiments, the kits of the present technology comprise multiple primer pairs that hybridize to one or more exons of a single gene selected from the group consisting of BRAF, PIK3R2, CNTNAP1, CTNNB1, SLIT1, NTRK3, HUWE1, CASKIN1, JMJD7, OR51T1, FAM20A, INHBA, OGDH, EPN3, LYPD2, SF3B1, APOD, CATSPER3, SEC16A, OR5T3, TANK, TAS1R3, RBPJL, ADAMTS16, PTAR1, PCDH20, BRCA2, WDR45, ATG4B, ZNF407, H6PD, NF2, BBS12, PSMD12, and TNN.

In certain embodiments, the kits of the present technology comprise multiple primer pairs comprising a single primer pair that specifically hybridizes to an exon of a single gene for each of BRAF, PIK3R2, CNTNAP1, CTNNB1, SLIT1, NTRK3, HUWE1, CASKIN1, JMJD7, OR51T1, FAM20A, INHBA, OGDH, EPN3, LYPD2, SF3B1, APOD, CATSPER3, SEC16A, OR5T3, TANK, TAS1R3, RBPJL, ADAMTS16, PTAR1, PCDH20, BRCA2, WDR45, ATG4B, ZNF407, H6PD, NF2, BBS12, PSMD12, and TNN.

In certain embodiments, the kits of the present technology comprise multiple primer pairs comprising more than one primer pair that hybridizes to one or more exons for each of BRAF, PIK3R2, CNTNAP1, CTNNB1, SLIT1, NTRK3, HUWE1, CASKIN1, OR51T1, FAM20A, INHBA, OGDH, EPN3, LYPD2, SF3B1, APOD, CATSPER3, SEC16A, OR5T3, TANK, TAS1R3, RBPJL, ADAMTS16, PTAR1, PCDH20, BRCA2, WDR45, ATG4B, ZNF407, H6PD, NF2, BBS12, PSMD12, and TNN.

Thus, it is contemplated herein that the kits of the present technology can comprise primer pairs that recognize and specifically hybridize to one or more exons of one or more genes selected from the group consisting BRAF, PIK3R2, CNTNAP1, CTNNB1, SLIT1, NTRK3, HUWE1, CASKIN1, JMJD7, OR51T1, FAM20A, INHBA, OGDH, EPN3, LYPD2, SF3B1, APOD, CATSPER3, SEC16A, OR5T3, TANK, TAS1R3, RBPJL, ADAMTS16, PTAR1, PCDH20, BRCA2, WDR45, ATG4B, ZNF407, H6PD, NF2, BBS12, PSMD12, and TNN.

Alternatively, the kit can comprise primer pairs that will detect one or more mutations selected from the group consisting of BRAF V600E, CTNNB1 S37C, CTNNB1 T41I or CTNNB1 S33C, PIK3R2 E593K, CNTNAP1 R270Q, SLIT1 H566R, NTRK3 V221I, HUWE1 S2039F, CASKIN1 P1196L, JMJD7L185F, OR51T1 R329H, FAM20A S119R, INHBA P291 S, OGDH I446F, EPN3 D458E, LYPD2 R24C, SF3B1 R625C, APOD D144Y, CATSPER3 E304A, SEC16A G1091R, OR5T3 L144H, TANK R394Q, TAS1R3 D307H, RBPJL L181P, ADAMTS16 P870S, PTAR1 D89A, PCDH20 D773H, BRCA2 P3067L, WDR45 R280C, ATG4B R49G, ZNF407 C120Y, H6PD P725T, NF2 Q324*, BBS12 R431P, PSMD12 I66V, or TAW L278V.

In some embodiments, the kits further comprise buffers, enzymes having polymerase activity, enzymes having polymerase activity and lacking 5'→3' exonuclease activity or both 5'→3' and 3'→5' exonuclease activity, enzyme cofactors such as magnesium or manganese, salts, chain extension nucleotides such as deoxynucleoside triphosphates (dNTPs), modified dNTPs, nuclease-resistant dNTPs or labeled dNTPs, necessary to carry out an assay or reaction, such as amplification and/or detection of alterations in target nucleic acid sequences corresponding to BRAF, PIK3R2, CNTNAP1, CTNNB1, SLIT1, NTRK3, HUWE1, CASKIN1, JMJD7, OR51T1, FAM20A, INHBA, OGDH, EPN3, LYPD2, SF3B1, APOD, CATSPER3, SEC16A, OR5T3, TANK, TAS1R3, RBPJL, ADAMTS16, PTAR1, PCDH20, BRCA2, WDR45, ATG4B, ZNF407, H6PD, NF2, BBS12, PSMD12, and TNN.

In one embodiment, the kits of the present technology further comprise a positive control nucleic acid sequence and a negative control nucleic acid sequence to ensure the integrity of the assay during experimental runs. A kit may further contain a means for comparing the levels and/or activity of one or more of BRAF, PIK3R2, CNTNAP1, CTNNB1, SLIT1, NTRK3, HUWE1, CASKIN1, JMJD7, OR51T1, FAM20A, INHBA, OGDH, EPN3, LYPD2, SF3B1, APOD, CATSPER3, SEC16A, OR5T3, TANK, TAS1R3, RBPJL, ADAMTS16, PTAR1, PCDH20, BRCA2, WDR45, ATG4B, ZNF407, H6PD, NF2, BBS12, PSMD12, and TNN in a tumor sample with a reference nucleic acid sample (e.g., a non-tumor sample). The kit may also comprise instructions for use, software for automated analysis, containers, packages such as packaging intended for commercial sale and the like.

The kits of the present technology can also include other necessary reagents to perform any of the NGS techniques disclosed herein. For example, the kit may further comprise one or more of: adapter sequences, barcode sequences, reaction tubes, ligases, ligase buffers, wash buffers and/or reagents, hybridization buffers and/or reagents, labeling buffers and/or reagents, and detection means. The buffers and/or reagents are usually optimized for the particular amplification/detection technique for which the kit is intended. Protocols for using these buffers and reagents for performing different steps of the procedure may also be included in the kit.

The kits of the present technology may include components that are used to prepare nucleic acids from an intracranial tumor test sample for the subsequent amplification and/or detection of alterations in target nucleic acid sequences corresponding to BRAF, PIK3R2, CNTNAP1, CTNNB1, SLIT1, NTRK3, HUWE1, CASKIN1, JMJD7, OR51T1, FAM20A, INHBA, OGDH, EPN3, LYPD2, SF3B1, APOD, CATSPER3, SEC16A, OR5T3, TANK, TAS1R3, RBPJL, ADAMTS16, PTAR1, PCDH20, BRCA2, WDR45, ATG4B, ZNF407, H6PD, NF2, BBS12, PSMD12, and TNN. Such sample preparation components can be used to produce nucleic acid extracts from tissue samples. The test samples used in the above-described methods will vary based on factors such as the assay format, nature of the detection method, and the specific tissues, cells or extracts used as the test sample to be assayed. Methods of extracting nucleic acids from samples are well known in the art and can be readily adapted to obtain a sample that is compatible with the system utilized. Automated sample preparation systems for extracting nucleic acids from a test sample are commercially available, e.g., Roche Molecular Systems' COBAS AmpliPrep System, Qiagen's BioRobot 9600, and Applied Biosystems' PRISM™ 6700 sample preparation system.

EXAMPLES

Example 1: Identification of Genetic Mutations Underlying Intracranial Neoplasms Tumor specimens and matched whole blood samples were obtained from patients undergoing medically recommended surgeries to treat a pituitary adenoma, meningioma, or a craniopharyngioma. Five craniopharyngioma tumors, three pituitary adenomas and one meningioma tumor were analyzed along with their corresponding matched whole blood control samples from each subject. Whole exome DNA sequencing libraries were generated from genomic DNA extracted from the fresh or frozen tumor tissues and the matched whole blood samples via Ion AmpliSeq Exome Kits. DNA libraries generated from normal (whole blood) and tumor tissue for each subject were tagged with separate barcodes to permit demultiplexing upon sequence analysis. One to two matched tumor-normal pairs of individual specimens were simultaneously sequenced on the Ion Proton™ system.

Whole Exome Sequencing (WES) results were analyzed using the AmpliSeq Exome tumor-normal pair workflow, which analyzes reads of a tumor sample and reads of the related normal sample to find somatic variants that appear in the tumor sample and not in the normal sample. It applies a binomial model (Poisson approximation) to determine if tumor variants are present in the normal sample above the error rate and is then assigned a somatic "confident" or "non-confident" designation. The workflow was modified to exclude variants in regions with 5 or more homopolymer stretches. Results were then filtered to include variants that were present only in the tumor tissues ("somatic confident"), with allele frequencies ≥10%. The selected variants were located in exonic or splice site regions that had an effect on protein sequence (i.e., non-synonymous), along with a predicted effect on protein function according to SIFT (≤0.05), PolyPhen (0.85-1.0), or Grantham (100-215) scoring. All known population polymorphisms with minor allele frequencies >0.01 were filtered out (annotation source 1000 Genomes Project). Additionally, the inclusion criteria required observation of a given variant in both read directions. Subsequent manual review of all remaining variants was performed to eliminate artifacts from the final results.

Four out of a total of five craniopharyngioma tumor-normal pairs yielded interpretable information. See Table 1.

TABLE 1

Mutations in Craniopharyngiomas

| Tumor/<br>Normal Pair | Freq<br>(%) | Dominant<br>Mutation | Function Pathways/Ontologies | Primary<br>Expression* |
|---|---|---|---|---|
| WES1-2 | 43 | BRAF V00E | RTK/MAPK signaling; postsynaptic responses of hippocampal neuron | Brain, testis |
|  | 41 | PIK3R2 E593K | RTK signalling pathways | Pancreas, ovary |
|  | 35 | CNTNAP1 R270Q | Axon Guidance (EGF-like domain) | Brain |
| WES3-4 | 25 | CTNNB1 S37C | WNT signaling is also involved in Axon guidance | Hair follicles, colon, cortical neurons |
|  | 16 | SLIT1 H566R | Axon Guidance (EGF-like domain) | Forebrain |
| WES7-8 | 44 | CTNNB1 T41I | WNT signaling is also involved in Axon guidance | Hair follicles, colon, cortical neurons |
|  | 34 | NTRK3 V221I | Neurotrophin binding (Protein Tyrosine Kinase) | Nervous tissue |
|  | 17 | HUWE1 S2039F | Protein monoubiquitination | Brain, heart, placenta |
|  | 26 | CASKIN1 P1196L | Signal Transduction (binds to neurexins and other cytoplasmic proteins) | Brain, Lung, Liver |
|  | 12 | JMJD7L185F | Not well characterized | Brain, skin |
| WES17-18 | 57 | CTNNB1 S33C | WNT signaling is also involved in Axon guidance | Hair follicles, colon, cortical neurons |
|  | 41 | OR51T1 R329H | GPCR; Olfaction, sensory transduction | Limited information |
|  | 38 | FAM20A S119R | Pseudokinase involved in calcium ion homeostasis | Lung, liver |
|  | 32 | INHBA P291S | Inhibition of pituitary hormone secretion | Vascular, placenta, umbilical cord |

*May also be expressed in other tissue, only the highest expression or primary expression is listed.

Table 1 demonstrates that genetic disruption of one or more of WNT, receptor tyrosine kinase, and MAPK signaling pathways may occur in craniopharyngioma specimens. Either BRAF or CTNNB1 mutations were identified in 100% of the craniopharyngioma specimens. Further, mutations in a variety of genes involved in neuronal signaling, axon guidance, pituitary hormone secretion, and protein ubiquitination were also present in craniopharyngiomas. See Table 1. The majority of the mutated genes in craniopharyngiomas that were observed in three of the four tumor-normal sets (WES1-2, WES3-4, and WEST-8) were those with primary or highest expression in the brain or nervous tissue.

Table 2 shows that two of the two prolactinoma specimens harbored the R625C mutation in the SF3B1 gene. Mutations in SF3B1 have also been reported in myelodysplastic syndrome (MDS) as well as a variety of other cancer types, including uveal melanoma. Zhu et al., *Leuk Res.* 44:8-16 (2016); Yavuzyigitoglu et al., *Ophthalmology* 123(5):1118-28 (2016). The presence of SF3B1 mutations in 100% of the assayed prolactinoma specimens suggests that SF3B1 mutations may be a key driver in prolactinoma tumors.

TABLE 2

Mutations in Prolactinomas, ACTH-producing Pituitary tumors, and Meningiomas

| Tumor/<br>Normal Pair | Tumor Type | Freq<br>(%) | Dominant<br>Mutation | Functional Pathways/Ontologies |
|---|---|---|---|---|
| WES11-12 | Prolactinoma | 71 | OGDH I446F | Cellular metabolism |
|  |  | 41 | EPN3 D458E | Clathrin coated vesicle componenet |
|  |  | 39 | LYPD 2R24C | Anchored plasma membrane protein |
|  |  | 39 | SF3B1 R625C | RNA splicing (mutated in MD S and multiple cancers) |
|  |  | 36 | APOD D144Y | Lipid transporter activity |
|  |  | 27 | CATSPER3 E304A | Cation channel |
|  |  | 26 | SEC16A G1091R | Vesicle-mediated transport |
|  |  | 21 | OR5T3 L144H | GPCR; Olfaction signaling |
| WES15-16 | Prolactinoma | 64 | TANK R394Q | NFKB pathway, innate immunity |
|  |  | 38 | TAS1R3 D307H | GPCR; Taste receptor |
|  |  | 23 | RBPJL L181P | Transcription regulation |
|  |  | 22 | ADAMTS16 P870S | Metalloendopeptidase; extra cellular matrix regulation |

TABLE 2-continued

Mutations in Prolactinomas, ACTH-producing Pituitary tumors, and Meningiomas

| Tumor/Normal Pair | Tumor Type | Freq (%) | Dominant Mutation | Functional Pathways/Ontologies |
|---|---|---|---|---|
| | | 19 | PTAR1 D89A | Protein prenylation |
| | | 17 | PCDH20 D773H | Cell adhesion |
| | | 16 | BRCA2 P3067L | DNA repair |
| | | 16 | WDR45 R280C | Autophagy (neurodegeneration) |
| | | 13 | SF3B1 R625C | RNA splicing (mutated in MD S and multiple cancers) |
| WES9-10 | ACTH producing pituitary tumor | 46 | ATG48 R49G | Peptidase involved in autophagy |
| | | 43 | ZNF407 C120Y | Zinc finger protein; possibly transcriptional regulation |
| | | 40 | H6PD P725T | Glucose metabolism |
| WES13-14 | Meningioma | 41 | NF2 Q324* | Tumor suppressor |
| | | 38 | BBS12 R431P | Membrane trafficking (Bardet-Biedl syndrome) |
| | | 21 | PSMD 12I66V | Proteasome (protein ubiquitination) |
| | | 12 | TNN L278V | Axonogenesis, cell growth/migration |

Additionally, mutations in genes involved in autophagy, metabolism, extracellular matrix proteins, cell signaling, and DNA repair (including BRCA2) were detected in the two prolactinomas and the single ACTH-producing pituitary tumor specimen. See Table 2.

Table 2 also shows that the meningioma sample harbored a NF2 Q324* nonsense mutation, which is known to be associated with meningiomas, ependymomas, and schwannomas. In addition to NF2, mutations in genes involved in membrane trafficking, protein ubiquitination, and cell migration were also identified.

These results suggest that the methods of the present technology are useful for selecting a subject with an intracranial neoplasm for treatment with one or more chemotherapeutic agents. For example, the methods disclosed herein are useful in predicting whether a subject with a prolactinoma will be responsive to treatment with a SF3b complex inhibitor. Further, the methods of the present technology are useful for selecting a subject with an intracranial neoplasm for combination therapy (e.g., treatment with a PI3K/AKT/mTOR pathway inhibitor and a BRAF inhibitor, or alternatively a WNT signaling pathway inhibitor and a GnRH antagonist).

EQUIVALENTS

The present technology is not to be limited in terms of the particular embodiments described in this application, which are intended as single illustrations of individual aspects of the present technology. Many modifications and variations of this present technology can be made without departing from its spirit and scope, as will be apparent to those skilled in the art. Functionally equivalent methods and apparatuses within the scope of the present technology, in addition to those enumerated herein, will be apparent to those skilled in the art from the foregoing descriptions. Such modifications and variations are intended to fall within the scope of the present technology. It is to be understood that this present technology is not limited to particular methods, reagents, compounds compositions or biological systems, which can, of course, vary. It is also to be understood that the terminology used herein is for the purpose of describing particular embodiments only, and is not intended to be limiting.

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like, include the number recited and refer to ranges which can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

All patents, patent applications, provisional applications, and publications referred to or cited herein are incorporated by reference in their entirety, including all FIGURES and tables, to the extent they are not inconsistent with the explicit teachings of this specification.

The invention claimed is:

1. A method for detecting at least one genetic mutation in a plurality of genes in an intracranial tumor sample of a subject comprising:
 (a) extracting DNA from a fresh or frozen intracranial tumor sample obtained from the subject;
 (b) generating a first library from the intracranial tumor sample, wherein the first library consists of amplicons corresponding to one or more genes associated with an intracranial tumor selected from PIK3R2, CNTNAP1, SLIT1, NTRK3, HUWE1, CASKIN1, JMJD7, OR51T1, FAM20A, INHBA, OGDH, EPN3, LYPD2, SF3B1, APOD, CATSPER3, SEC16A, OR5T3, TANK, TAS1R3, RBPJL, ADAMTS16, PTAR1, PCDH20, BRCA2, WDR45, ATG4B, ZNF407, H6PD, NF2, BBS12, PSMD12, TNN, BRAF and CTNNB1;
(c) ligating an adapter sequence comprising a barcode sequence to the ends of the amplicons corresponding to the plurality of genes; and
(d) determining the presence of at least one genetic mutation in the amplicons of the plurality of genes using high throughput massive parallel sequencing,
wherein the intracranial tumor is a pituitary adenoma, meningioma, or craniopharyngioma.

2. The method of claim 1, further comprising detecting a BRAF mutation or a CTNNB1 mutation in the amplicons corresponding to the plurality of genes.

3. The method of claim 2, wherein the BRAF mutation is BRAF V600E or wherein the CTNNB1 mutation is CTNNB1 S37C, CTNNB1 T41I or CTNNB1 S33C.

4. The method of claim 1, wherein the pituitary adenoma is prolactin-secreting or ACTH-secreting or is not associated with a mutation in AIP or MEN1.

5. The method of claim 1, wherein the craniopharyngioma is papillary or adamantinomatous.

6. The method of claim 1, wherein the at least one genetic mutation is selected from PIK3R2 E593K, CNTNAP1 R270Q, SLIT1 H566R, NTRK3 V221I, HUWE1 S2039F, CASKIN1 P1196L, JMJD7 L185F, OR51T1 R329H, FAM20A S119R, INHBA P291S, OGDH I446F, EPN3 D458E, LYPD2 R24C, SF3B1 R625C, APOD D144Y, CATSPER3 E304A, SEC16A G1091R, OR5T3 L144H, TANK R394Q, TAS1R3 D307H, RBPJL L181P, ADAMTS16 P870S, PTAR1 D89A, PCDH2O D773H, BRCA2 P3067L, WDR45 R280C, ATG4B R49G, ZNF407 C120Y, H6PD P725T, NF2 Q324*, BBS12 R431P, PSMD12 I66V, or TNN L278V.

7. The method of claim 1, further comprising
(e) extracting DNA from a control tissue sample obtained from the subject;
(f) generating a second library from the control tissue sample comprising amplicons of the plurality of genes; and
(g) ligating a second adaptor sequence comprising a second barcode sequence to the ends of the amplicons corresponding to the plurality of gene.

8. The method of claim 7, wherein at least one genetic mutation is detected in the first library, and the at least one genetic mutation is not detected in the second library.

9. The method of claim 7, wherein the control tissue sample is a matched whole blood sample from the subject.

* * * * *